US012702236B2

(12) United States Patent
Johnston et al.

(10) Patent No.: US 12,702,236 B2
(45) Date of Patent: Aug. 11, 2026

(54) USING FORCE SENSORS IN BED SYSTEMS

(71) Applicant: Sleep Number Corporation, Minneapolis, MN (US)

(72) Inventors: Robert Dean Johnston, Lakeville, MN (US); Gary N. Garcia Molina, DeForest, WI (US); Cory Lee Grabinger, Maple Grove, MN (US); Ajdin Mulaosmanovic, Sarajevo (BA); Megha Rajam Rao, San Jose, CA (US)

(73) Assignee: Sleep Number Corporation

( * ) Notice: Subject to any disclaimer, the term of this patent is extended or adjusted under 35 U.S.C. 154(b) by 182 days.

(21) Appl. No.: 18/389,388

(22) Filed: Nov. 14, 2023

(65) Prior Publication Data

US 2024/0164533 A1 May 23, 2024

Related U.S. Application Data

(60) Provisional application No. 63/426,119, filed on Nov. 17, 2022.

(51) Int. Cl.

| | |
|---|---|
| ***A47C 19/22*** | (2006.01) |
| ***A47C 19/02*** | (2006.01) |
| ***A61B 5/00*** | (2006.01) |
| ***G01G 19/52*** | (2006.01) |

(52) U.S. Cl.

CPC ............ *A47C 19/22* (2013.01); *A47C 19/024* (2013.01); *A47C 19/025* (2013.01); *G01G 19/52* (2013.01); *A61B 5/6892* (2013.01)

(58) Field of Classification Search

CPC ..... A47C 19/22; A47C 19/024; A47C 19/025; G01G 19/52; A61B 5/6892; A61B 2562/0261; A61B 5/6891; A61B 5/1115; A61B 5/4806; A61G 7/0527

See application file for complete search history.

(56) References Cited

U.S. PATENT DOCUMENTS

| | | | |
|---|---|---|---|
| 411,343 | A | 9/1889 | Benjamine |
| 2,990,899 | A | 7/1961 | De Bella |
| 3,287,745 | A | 11/1966 | Maddox |
| 3,338,323 | A | 8/1967 | Swersey |
| 3,360,032 | A | 12/1967 | Potter |
| 3,722,611 | A | 3/1973 | Tirkkonen |
| 4,023,633 | A | 5/1977 | Swersey et al. |
| 4,121,453 | A | 10/1978 | Levin et al. |
| 4,281,730 | A | 8/1981 | Swersey et al. |

(Continued)

FOREIGN PATENT DOCUMENTS

| | | |
|---|---|---|
| AU | 2012101423 | 10/2012 |
| DE | 2020/07019717 | 11/2016 |

(Continued)

OTHER PUBLICATIONS

U.S. Appl. No. 16/719,177, Nunn et al., filed Dec. 18, 2019.

(Continued)

*Primary Examiner* — Matthew Troutman
*Assistant Examiner* — Alison N Labarge
(74) *Attorney, Agent, or Firm* — Norton Rose Fulbright US LLP

(57) ABSTRACT

A bed system includes a support platform and a plurality of legs supporting the support platform. Each leg of the plurality of legs includes a force sensor that is configured to sense a force applied to the leg.

19 Claims, 21 Drawing Sheets

(56) References Cited

U.S. PATENT DOCUMENTS

| | | | | |
|---|---|---|---|---|
| 4,551,882 | A | 11/1985 | Swersey et al. | |
| 4,633,237 | A | 12/1986 | Tucknott et al. | |
| 4,667,357 | A | 5/1987 | Fortune | |
| 4,679,569 | A | 7/1987 | Lee | |
| 4,793,428 | A | 12/1988 | Swersey | |
| 4,974,692 | A | 12/1990 | Carruth et al. | |
| 5,173,977 | A | 12/1992 | Carruth et al. | |
| 5,184,112 | A | 2/1993 | Gusakov | |
| 5,276,432 | A | 1/1994 | Travis | |
| 5,393,935 | A | 2/1995 | Hasty et al. | |
| 5,393,938 | A | 2/1995 | Bumbalough | |
| 5,747,745 | A | 5/1998 | Neuman | |
| 5,831,221 | A | 11/1998 | Geringer | |
| 5,861,582 | A | 1/1999 | Flanagan et al. | |
| 6,280,392 | B1 | 8/2001 | Yoshimi et al. | |
| 6,639,157 | B2 | 10/2003 | Sternberg | |
| 6,680,442 | B1 | 1/2004 | Rynd et al. | |
| 6,761,683 | B2 | 7/2004 | Gryn et al. | |
| 6,765,154 | B2 | 7/2004 | Sternberg | |
| 6,822,571 | B2 | 11/2004 | Conway | |
| 6,852,086 | B2 | 2/2005 | Atlas | |
| 7,176,391 | B2 | 2/2007 | Metz et al. | |
| 7,253,366 | B2 | 8/2007 | Bhai | |
| 7,335,839 | B2 | 2/2008 | Metz et al. | |
| 7,437,787 | B2 | 10/2008 | Bhai | |
| 7,467,426 | B1 | 12/2008 | Jarmon | |
| 8,048,005 | B2 | 11/2011 | Dixon et al. | |
| 8,262,582 | B2 | 9/2012 | Kortelainen | |
| 8,279,057 | B2 | 10/2012 | Hirose | |
| 8,376,964 | B2 | 2/2013 | Park et al. | |
| 8,444,558 | B2 | 5/2013 | Young et al. | |
| 8,469,884 | B2 | 6/2013 | David et al. | |
| 8,491,490 | B2 | 7/2013 | Ozaki et al. | |
| 8,544,347 | B1 | 10/2013 | Berme | |
| 8,672,853 | B2 | 3/2014 | Young | |
| 8,821,418 | B2 | 9/2014 | Meger et al. | |
| 8,984,687 | B2 | 3/2015 | Stusynski et al. | |
| 9,013,313 | B2 | 4/2015 | Paine | |
| 9,370,457 | B2 | 6/2016 | Nunn et al. | |
| 9,383,251 | B2 | 7/2016 | Dixon et al. | |
| 9,392,879 | B2 | 7/2016 | Nunn et al. | |
| 9,445,751 | B2 | 9/2016 | Young et al. | |
| 9,504,416 | B2 | 11/2016 | Young et al. | |
| 9,506,106 | B2 | 11/2016 | Gough et al. | |
| 9,510,688 | B2 | 12/2016 | Nunn et al. | |
| 9,596,998 | B2 | 3/2017 | Muehlsteff et al. | |
| 9,635,953 | B2 | 5/2017 | Nunn et al. | |
| 9,679,462 | B1 | 6/2017 | Robertson | |
| 9,770,114 | B2 | 9/2017 | Brosnan et al. | |
| 9,844,275 | B2 | 12/2017 | Nunn et al. | |
| 9,931,085 | B2 | 4/2018 | Young et al. | |
| D818,383 | S | 5/2018 | Sato et al. | |
| 10,058,467 | B2 | 8/2018 | Stusynski et al. | |
| 10,092,242 | B2 | 10/2018 | Nunn et al. | |
| 10,149,549 | B2 | 12/2018 | Erko et al. | |
| 10,182,661 | B2 | 1/2019 | Nunn et al. | |
| 10,201,234 | B2 | 2/2019 | Nunn et al. | |
| 10,206,590 | B2 | 2/2019 | Meriheina | |
| 10,251,490 | B2 | 4/2019 | Nunn et al. | |
| 10,342,358 | B1 | 7/2019 | Palashewski et al. | |
| 10,413,233 | B2 | 9/2019 | Meriheina | |
| 10,441,086 | B2 | 10/2019 | Nunn et al. | |
| 10,441,087 | B2 | 10/2019 | Karschnik et al. | |
| 10,448,749 | B2 | 10/2019 | Palashewski et al. | |
| 10,492,969 | B2 | 12/2019 | Stusynski et al. | |
| 10,632,032 | B1 | 4/2020 | Stusynski et al. | |
| 10,646,050 | B2 | 5/2020 | Nunn et al. | |
| 10,674,832 | B2 | 6/2020 | Brosnan et al. | |
| 10,716,512 | B2 | 7/2020 | Erko et al. | |
| 10,729,255 | B2 | 8/2020 | Erko et al. | |
| 10,736,432 | B2 | 8/2020 | Brosnan et al. | |
| 10,750,875 | B2 | 8/2020 | Palashewski et al. | |
| 10,827,846 | B2 | 11/2020 | Karschnik et al. | |
| 10,881,219 | B2 | 1/2021 | Nunn et al. | |
| 10,957,335 | B2 | 3/2021 | Demirli et al. | |
| 10,959,535 | B2 | 3/2021 | Karschnik et al. | |
| D916,745 | S | 4/2021 | Stusynski et al. | |
| 10,980,351 | B2 | 4/2021 | Nunn et al. | |
| 11,096,849 | B2 | 8/2021 | Stusynski et al. | |
| 11,122,909 | B2 | 9/2021 | Palashewski et al. | |
| 11,160,683 | B2 | 11/2021 | Nunn et al. | |
| 11,206,929 | B2 | 12/2021 | Palashewski et al. | |
| D954,725 | S | 6/2022 | Stusynski et al. | |
| D968,436 | S | 11/2022 | Stusynski et al. | |
| D975,121 | S | 1/2023 | Stusynski et al. | |
| D1,000,464 | S | 10/2023 | Stusynski et al. | |
| D1,018,476 | S | 3/2024 | Dixon et al. | |
| 2002/0023785 | A1 | 2/2002 | Sternberg | |
| 2002/0070867 | A1 | 6/2002 | Conway et al. | |
| 2003/0140714 | A1 | 7/2003 | Barua et al. | |
| 2003/0233034 | A1 | 12/2003 | Varri et al. | |
| 2006/0129047 | A1 | 6/2006 | Ruotoistenmaki | |
| 2006/0175097 | A1 | 8/2006 | Pirzada | |
| 2007/0161917 | A1 | 7/2007 | Ozaki et al. | |
| 2007/0191742 | A1 | 8/2007 | Park | |
| 2008/0077020 | A1 | 3/2008 | Young et al. | |
| 2010/0170043 | A1 | 7/2010 | Young et al. | |
| 2011/0004435 | A1 | 1/2011 | Lindstrom et al. | |
| 2011/0046498 | A1* | 2/2011 | Klap .................... | A61B 5/0205 600/534 |
| 2011/0144455 | A1 | 6/2011 | Young et al. | |
| 2012/0078573 | A1 | 3/2012 | Kazuno | |
| 2012/0184862 | A1 | 7/2012 | Foo et al. | |
| 2013/0135137 | A1 | 5/2013 | Mulder et al. | |
| 2013/0146371 | A1 | 6/2013 | Shih | |
| 2013/0174345 | A1 | 7/2013 | Leu et al. | |
| 2014/0069729 | A1 | 3/2014 | Shih | |
| 2014/0135635 | A1 | 5/2014 | Vanderpohl | |
| 2014/0277822 | A1 | 9/2014 | Nunn et al. | |
| 2014/0352060 | A1 | 12/2014 | Hirose | |
| 2015/0101870 | A1 | 4/2015 | Gough et al. | |
| 2015/0126818 | A1 | 5/2015 | Fung et al. | |
| 2015/0157258 | A1 | 6/2015 | Beattie et al. | |
| 2015/0238021 | A1 | 8/2015 | Wassermann | |
| 2015/0320229 | A1 | 11/2015 | Edling et al. | |
| 2016/0015184 | A1 | 1/2016 | Nunn et al. | |
| 2016/0051156 | A1 | 2/2016 | Kim | |
| 2016/0063846 | A1 | 3/2016 | Lemire et al. | |
| 2016/0235367 | A1 | 8/2016 | Kolar et al. | |
| 2016/0367039 | A1 | 12/2016 | Young et al. | |
| 2017/0065220 | A1 | 3/2017 | Young et al. | |
| 2017/0067774 | A1* | 3/2017 | Gough ................. | A61G 7/0527 |
| 2017/0128001 | A1 | 5/2017 | Torre et al. | |
| 2017/0143269 | A1 | 5/2017 | Young et al. | |
| 2017/0160709 | A1 | 6/2017 | Yang | |
| 2017/0312154 | A1 | 11/2017 | Kubiak et al. | |
| 2018/0008168 | A1* | 1/2018 | Pearlman ............... | A61B 5/002 |
| 2018/0098900 | A1* | 4/2018 | Sato ..................... | A61G 7/0527 |
| 2018/0132627 | A1 | 5/2018 | Van Erlach | |
| 2019/0053761 | A1 | 2/2019 | Torre et al. | |
| 2019/0069840 | A1 | 3/2019 | Young et al. | |
| 2019/0200777 | A1 | 7/2019 | Demirli et al. | |
| 2019/0201265 | A1 | 7/2019 | Sayadi et al. | |
| 2019/0201266 | A1 | 7/2019 | Sayadi et al. | |
| 2019/0201267 | A1 | 7/2019 | Demirli et al. | |
| 2019/0201268 | A1 | 7/2019 | Sayadi et al. | |
| 2019/0201270 | A1 | 7/2019 | Sayadi et al. | |
| 2019/0201271 | A1 | 7/2019 | Grey et al. | |
| 2019/0290147 | A1 | 9/2019 | Persen | |
| 2019/0328146 | A1 | 10/2019 | Palashewski et al. | |
| 2019/0328147 | A1 | 10/2019 | Palashewski et al. | |
| 2020/0060558 | A1 | 2/2020 | Aleksov | |
| 2020/0107753 | A1* | 4/2020 | Young .................. | A61B 5/7415 |
| 2020/0109985 | A1 | 4/2020 | Young et al. | |
| 2020/0110194 | A1 | 4/2020 | Young et al. | |
| 2020/0158560 | A1 | 5/2020 | Khair | |
| 2020/0163627 | A1 | 5/2020 | Sayadi et al. | |
| 2020/0253383 | A1 | 8/2020 | Young et al. | |
| 2020/0315367 | A1 | 10/2020 | Demirli et al. | |
| 2020/0336010 | A1 | 10/2020 | Holmvik et al. | |
| 2020/0337470 | A1 | 10/2020 | Sayadi et al. | |
| 2020/0359807 | A1 | 11/2020 | Brosnan et al. | |
| 2020/0367663 | A1 | 11/2020 | Nunn et al. | |
| 2020/0405070 | A1 | 12/2020 | Palashewski et al. | |

(56) References Cited

U.S. PATENT DOCUMENTS

| | | | |
|---|---|---|---|
| 2020/0405240 | A1 | 12/2020 | Palashewski et al. |
| 2021/0000261 | A1 | 1/2021 | Erko et al. |
| 2021/0034989 | A1 | 2/2021 | Palashewski et al. |
| 2021/0045541 | A1 | 2/2021 | Nunn et al. |
| 2021/0068552 | A1 | 3/2021 | Palashewski et al. |
| 2021/0112992 | A1 | 4/2021 | Nunn et al. |
| 2021/0267380 | A1 | 9/2021 | Stusynski |
| 2021/0282570 | A1 | 9/2021 | Karschnik et al. |
| 2021/0289947 | A1 | 9/2021 | Karschnik et al. |
| 2021/0314405 | A1 | 10/2021 | Demirli et al. |
| 2021/0346218 | A1 | 11/2021 | Stusynski et al. |
| 2022/0000273 | A1 | 1/2022 | Palashewski et al. |
| 2022/0000654 | A1 | 1/2022 | Nunn et al. |
| 2022/0031220 | A1 | 2/2022 | Guidoboni |
| 2022/0225786 | A1 | 7/2022 | Palashewski et al. |
| 2022/0265059 | A1 | 8/2022 | Palashewski et al. |
| 2022/0305231 | A1 | 9/2022 | Stusynski et al. |
| 2022/0346565 | A1 | 11/2022 | Karschnik et al. |
| 2022/0354431 | A1 | 11/2022 | Molina et al. |
| 2022/0364905 | A1 | 11/2022 | Young et al. |
| 2022/0386947 | A1 | 12/2022 | Molina et al. |
| 2022/0395233 | A1 | 12/2022 | Siyahjani et al. |
| 2023/0018558 | A1 | 1/2023 | Demirli et al. |
| 2023/0021928 | A1 | 1/2023 | Young et al. |
| 2023/0035257 | A1 | 2/2023 | Karschnik et al. |
| 2023/0037482 | A1 | 2/2023 | Demirli et al. |
| 2023/0054736 | A1 | 2/2023 | Holmvik et al. |
| 2023/0063373 | A1 | 3/2023 | Young et al. |
| 2023/0142604 | A1 | 5/2023 | Dixon et al. |
| 2023/0148762 | A1 | 5/2023 | Karschnik et al. |
| 2023/0181104 | A1 | 6/2023 | Johnston et al. |
| 2023/0190199 | A1 | 6/2023 | Molina |
| 2023/0210256 | A1 | 7/2023 | MacLachlan et al. |
| 2023/0210268 | A1 | 7/2023 | Kirk et al. |
| 2023/0210269 | A1 | 7/2023 | Hill et al. |
| 2023/0210274 | A1 | 7/2023 | Hill et al. |
| 2023/0210275 | A1 | 7/2023 | Hill et al. |
| 2023/0218093 | A1 | 7/2023 | Nunn et al. |
| 2023/0225517 | A1 | 7/2023 | Sayadi et al. |
| 2023/0255843 | A1 | 8/2023 | Sayadi et al. |
| 2023/0273066 | A1 | 8/2023 | Young et al. |
| 2023/0363963 | A1 | 11/2023 | Sayadi et al. |
| 2023/0380756 | A1 | 11/2023 | Palashewski et al. |
| 2023/0404282 | A1 | 12/2023 | Sayadi et al. |
| 2023/0404825 | A1 | 12/2023 | Stusynski et al. |
| 2023/0412683 | A1 | 12/2023 | Demirli et al. |
| 2024/0016302 | A1 | 1/2024 | Brosnan et al. |
| 2024/0032705 | A1 | 2/2024 | Nunn et al. |
| 2024/0041221 | A1 | 2/2024 | Blomseth et al. |
| 2024/0041677 | A1 | 2/2024 | Grey et al. |
| 2024/0091487 | A1 | 3/2024 | Molina et al. |
| 2024/0138579 | A1 | 5/2024 | Karschnik et al. |

FOREIGN PATENT DOCUMENTS

| | | | | |
|---|---|---|---|---|
| EP | 0218957 | | 4/1987 | |
| EP | 1635153 | | 3/2008 | |
| EP | 2148179 | A1 * | 1/2010 | ........... A61B 5/1102 |
| EP | 2805702 | | 11/2014 | |
| EP | 1937148 | | 1/2015 | |
| FI | 116097 | | 9/2005 | |
| GB | 2119528 | | 11/1983 | |
| JP | H07198224 | | 3/1995 | |
| JP | 2002-182270 | | 6/2002 | |
| JP | 2004-024370 | | 1/2004 | |
| JP | 4002905 | | 11/2007 | |
| JP | 2012-207798 | | 10/2012 | |
| JP | 2014066573 | A * | 4/2014 | |
| JP | 2014-233485 | | 12/2014 | |
| JP | 2014-235090 | | 12/2014 | |
| KR | 20060092037 | | 8/2006 | |
| KR | 10-2011-0033102 | | 3/2011 | |
| KR | 10-2012-0045660 | | 5/2012 | |
| KR | 10-2012-0119684 | | 10/2012 | |
| KR | 20120119684 | | 10/2012 | |
| KR | 101798498 | | 11/2017 | |
| WO | WO 1999/017658 | | 4/1999 | |
| WO | WO 2007/042960 | | 4/2007 | |
| WO | WO 2011/009085 | | 1/2011 | |
| WO | WO 2013/181474 | | 12/2013 | |
| WO | WO 2015/008677 | | 1/2015 | |
| WO | WO 2015/089274 | | 6/2015 | |
| WO | WO 2017/199944 | | 11/2017 | |
| WO | WO 2018/079403 | | 5/2018 | |
| WO | WO 2020/076423 | | 4/2020 | |
| WO | WO 2020/102383 | | 5/2020 | |

OTHER PUBLICATIONS

U.S. Appl. No. 17/745,508, Nunn et al., filed May 16, 2022.
U.S. Appl. No. 18/404,647, Palashewski et al., filed Jan. 4, 2024.
U.S. Appl. No. 18/416,387, Nunn et al., filed Jan. 18, 2024.
U.S. Appl. No. 18/433,289, Demirli et al., filed Feb. 5, 2024.
U.S. Appl. No. 18/538,884, Palashewski et al., filed Dec. 13, 2023.
U.S. Appl. No. 18/602,407, Holmvik et al., filed Mar. 12, 2024.
U.S. Appl. No. 18/604,949, Palashewski et al., Mar. 14, 2024.
U.S. Appl. No. 18/639,292, Mayandi et al., filed Apr. 18, 2024.
U.S. Appl. No. 18/643,648, Sohn et al., filed Apr. 23, 2024.
U.S. Appl. No. 29/881,955, filed Jan. 9, 2023, Stusynski et al.
U.S. Appl. No. 29/910,800, filed Aug. 24, 2023, Stusynski et al.
U.S. Appl. No. 29/924,373, filed Jan. 18, 2024, Dixon et al.
Adami et al., "A Gaussian model for movement detection during sleep," Annu Int Cont IEEE Eng Med Biol Soc 2012, 2012:2263-6.
Adami et al., "A method for classification of movements in bed," Annu Int Conf IEEE Eng Med Biol Soc 2011, 2011, 7881-4 (abstract only).
Adami et al., "A subject state detection approach to determine rest-activity pattems using load cells," Annu Int Cont IEEE Eng Med Biol Soc. 2010, 2010:204-7.
Adami et al., "A System for Unobtrusive Monitoring of Mobility in Bed," 2008 11th IEEE International Conference on Computational Science and Engineering—Workshops, San Paulo, 2008, pp. 13-18 (abstract only).
Adami et al., "Assessment and Classification of Movements in Bed Using Unobtrustive Sensors Dissertation," ProQuest Information and Learning Company, Aug. 2006, 24 pages.
Adami et al., "Comparison of load cells and wrist-actigraphy for unobtrusive monitoring of sleep movements," Annu Int Cont IEEE Eng Med Biol Soc. 2009, 2009:1314-7.
Adami et al., "Detection and Classification of Movements in Bed using Load Cells," Cont Proc IEEE Eng Med Biol Soc 2005, 2006:589-92 (abstract only).
Adami et al., "Detection of Movement in Bed Using Unobtrusive Load Cell Sensors," in IEEE Transactions on Information Technology in Biomedicine, Mar. 2010, vol. 14, No. 2, pp. 481-490 (abstract only).
Adami et al., "Unobtrusive monitoring of sleep patterns," Proceedings of the 25th Annual Intemational Conference of the IEEE Engineering in Medicine and Biology Society (IEEE Cat. No. 03CH37439), Cancun, 2003, vol. 2, pp. 1360-1363 (abstract only).
Adami et al., "Unobtrusive Movement Detection during Sleep based on Load Cell Dynamics," 2013, 9 pages.
Adami et al., "Using load cells under the bed as a non-contact rnethod for detecting periodic leg movements," 2014, IRBM. 35.10. 1016/j.irbm.2014, 1 page.
Alaziz et al., "Motion Scale: A Body Motion Monitoring System Using Bed-Mounted Wireless Load Cells," 2016 IEEE First International Conference on Connected Health: Applications, Systems and Engineering Technologies (CHASE), Washington, DC, 2016, pp. 183-192.
Alihanka et al., "A new method for long-term monitoring of the ballistocardiogram, heart rate, and respiration," American Journal of Physiology-Regulatory, Integrative and Comparative Physiology, 1981, R384-R392 (abstract only).
Alihanka et al., "A static charge sensitive bed. A new method for recording body movements during sleep," Electroencephalography and Clinical Neurophysiology, vol. 46, Issue 6, 1979, pp. 731-734 (abstract only).

(56) References Cited

OTHER PUBLICATIONS

Alivar et al., "Motion Detection in Bed-Based Ballistocardiogram to Quantify Sleep Quality," GLOBECOM 2017-2017 IEEE Global Communications Conference, Singapore, 2017, 6 pages.
Aung Aung et al., "Evaluation and analysis of multimodal sensors for developing in and around the bed patient monitoring system," 2010 Annual International Conference of the IEEE Engineering in Medicine and Biology, Buenos Aires, 2010, pp. 2159-2162 (abstract only).
Austin et al. "Unobtrusive classification of sleep and wakefulness using load cells under the bed," Annual International Conference of the IEEE Engineering in Medicine and Biology Society, IEEE Engineering in Medicine and Biology Society. Annual International Conference vol. 2012, 5254-7.
Beattie et al., "A time-frequency respiration tracking system using non-contact bed sensors with harmonic artifact rejection," Annu Int Cont IEEE Eng Med Biol Soc. Aug. 2015, 2015:8111-4.
Beattie et al., "Accurate scoring of the apnea-hypopnea index using a simple non-contact breathing sensor," J Sleep Res. Jun. 2013; 22(3):356-62.
Beattie et al., "Classification of Breathing Events Using Load Cells under the Bed," Cont Proc IEEE Eng Med Biol Soc. 2009, 2009: 3921-3924.
Beattie et al., "Classification of lying position using load cells under the bed," Annu Int Conf IEEE Eng Med Biol Soc. 2011, 2011:474-7.
Bio-Physical Signal, Advanced Biometric Research Center, Department of Biomedical Engineering, College of Medicine, Seoul National University, 2015, 4 pages <http://abrc.snu.ac.kr/korean/viewtopic.php?p=4039>.
Braunstein et al. "Design of a two-dimensional ballistocardiograph," The Journal of clinical investigation vol. 29.9 (1950): 1219-26.
Brink et al., "Contact-free measurement of heart rate, respiration rate, and body movements during sleep," Behavior Research Methods 38, 511-521 (2006).
Brotmacher, "The normal ballistocardiogram," Br Heart Journal, Apr. 1956, 18(2):145-52.
Carlson et al., "Bed-based instrumentation or unobtrusive sleep quality assessment in severely disabled autistic children," Annu Int Cont IEEE Eng Med Biol Soc, Aug. 2016, 2016:4909-4912 (abstract only).
Carlson, "Development of a bed-based nighttime monitoring toolset Dissertation," Kansas State University, May 2019, <https://krex.k-state.edu/dspace/handle/2097/39650>, 154 pages (abstract only).
Chamadiya et al., "Textile-Based, Contactless ECG Monitoring for Non-ICU Clinical Settings," Journal of Ambient Intelligence and Humanized Computing, Jul. 2012, 11 pages.
Choi et al., "Non-constraining sleep/wake monitoring system using bed actigraphy," Med Biol Eng Comput, Jan. 2007, 45(1):107-14 (abstract only).
Choi et al., "Slow-wave sleep estimation on a load-cell-installed bed: a non-constrained method," Physiol Meas, Nov. 2009, 30(11):1163-70 (abstract only).
Chung et al., "Noninvasive heart rate variability analysis using loadcell-installed bed during sleep," Annu Int Cont IEEE Eng Med Biol Soc. 2007, 2007:2357-60 (abstract only).
Chung et al., "Wakefulness estimation only using ballistocardiogram: nonintrusive method for sleep monitoring," Annu Int Cont IEEE Eng Med Biol Soc. 2010, 2010:2459-62.
Di Lecce et al., "Smart Postural Monitor for Elderly People," Jul. 2013, 4 pages.
Extended European Search Report in European Appln No. 19870848.9, dated Mar. 20, 2023, 13 pages.
Gordon, "Certain Molar Movements of the Human Body produced by the Circulation of the Blood," J Anal Physiol, 1877, 11(Pt 3):533-536.
Intemational Search Report and Written Opinion of corresponding International Application No. PCT/US2019/055121; mailed Jan. 23, 2020, 11 pages.
International Search Report and Written Opinion in International Appln. No. PCT/US2023/037254, mailed on Feb. 28, 2024, 25 pages.
Jung et al., "Estimation of sleep onset latency based on the blood pressure regulatory reflex mechanism.," IEEE J Biomed Health Inform, May 2013,17(3):534-44 (abstract only).
Jung et al., "Nocturnal Awakening and Sleep Efficiency Estimation Using Unobtrusively Measured Ballistocardiogram," IEEE Transactions on Biomedical Engineering, Jan. 2014, vol. 61, No. 1, pp. 131-138.
Kim et al., "Ballistocardiogram: Mechanism and Potential for Unobtrusive Cardiovascular Health Monitoring," Sci Rep 6, Aug. 2016, 6 pages.
Lee et al., "Ballistocardiogram of baby during sleep," Annu Int Conf IEEE Eng Med Biol Soc. 2015, 2015:7167-70 (abstract only).
Lee et al., Physiological Signal Monitoring Bed for Infants Based on Load-Cell Sensors, Sensors, 2016, 16,409, 19 pages.
Load Cell Central website, "Hospital Beds, Portable Carts, Table Load Cell System," <https://www.800loadcell.com/special-applications/other-specialized-systems/custom-load-cell-5.html, available on or before Nov. 2020, 3 pages.
Loadstar Sensors Website, "Monitor Sleep Patterns," retrieved from URL<https://www.loadstarsensors.com/monitor-sleep-patterns.html>, accessed Nov. 2020, 1 page.
March, "Three-Plane Ballistocardiography: The Effect of Age on the Longitudinal, Lateral, and Dorsoventral Ballistocardiograms," Circulation. 1955, 12:869-882, 14 pages.
Mietus et al., "Detection of obstructive sleep apnea from cardiac interbeat interval time series," Computers in Cardiology 2000. vol. 27 (Cat. 00CH37163), Cambridge, MA, 2000, pp. 1753-1756.
Muller, Projekt NEMESIS Niederfrequente elektrische und magnetische Felder und Elektrosensibilitat in der Schweiz; Doctoral Thesis; 2000; ETH Zurich Research collection (English summary only).
Nagura et al., "A practical BCG measuring system with bed sensors and algorithm for heartbeat detection," 2018 IEEE 15th International Workshop on Advanced Motion Control (AMC), Tokyo, 2018, pp. 317-321 (abstract only).
Nagura et al., "An estimation of heart rate variability from ballistocardiogram measured with bed leg sensors," 2018 IEEE International Conference on Industrial Technology (ICIT), Lyon, 2018, pp. 2005-2009.
Nehmer el al., The Intelligent Bed—Ambient Monitoring of Sick and Disabled Persons through the Use of Load Sensors in Bed Legs, ERCIM News 87, Oct. 13, 2011, pp. 26-27, https://ercim-news.ercim.eu/en87/special/thentelligent-bed.
Nihon Kohden [website], "History—1950's, product—MB-1 Ballistocardiograph," 1953, <https://www.nihonkohden.com/company/history/1950s.html>, available on or before Nov. 2020, 5 pages.
Noh et al., "BCG Monitoring System using Unconstrained Method with Daubechies Wavelet Transform," Inter. Cont. on IML 2009, pp. 338-344.
Nukaya et al., "Noninvasive Bed Sensing of Human Biosignals Via Piezoceramic Devices Sandwiched Between the Floor and Bed," IEEE Sensors Journal, Mar. 2012, 12(3), 8 pages.
Pinheiro et al., "Study on Ballistocardiogram Acquisition in a Moving Wheelchair with Embedded Sensors," Metrology and Measurement Systems, 2012, 739-750.
Ricoh Website, "Bed Sensor," announced 2017, retrieved from URL<https://www.ricoh.com/about/empowering-digital-workplaces/articles/innovations-vital-to-enhancing-long-term-care>, accessed Nov. 2020, 9 pages.
Rosales et al., "Heartbeat detection from a hydraulic bed sensor using a clustering approach," Annu Int Cont IEEE Eng Med Biol Soc. 2012;2012:2383-7 (abstract only).
Sadek et al., "Ballistocardiogram signal processing: a review," Health Inf Sci Syst 7, May 2019, 23 pages.
Schrempf et al., "Measuring nightly activity, body weight and body weight change rate with a sensor equipped bed," Annu Int Cont IEEE Eng Med Biol Soc. 2010;2010:2151-4 (abstract only).
Sensotech Website; Patient Monitoring Sensors—Load Cell for Bed Weighing; https://www.sensomaticloadcell.in/patient-monitoring-sensor.html; accessed Nov. 2020, 2 pages.

(56) References Cited

OTHER PUBLICATIONS

Shin et al., “Automatic ballistocardiogram (BCG) beat detection using a template matching approach,” Annu Int Cont IEEE Eng Med Biol Soc. 2008, 2008:1144-6 (abstract only).
Starr et al., “Twenty-Year Studies with the Ballistocardiograph: The Relation between the Amplitude of the First Record of “Healthy” Adults and Eventual Mortality and Morbidity from Heart Disease,” Circulation, 1961, 23:714-732.
Stryker Maintenance Manual, “MedSurge Bed Model 3002 S3 Patriot Series,” Oct. 2008, retrieved from URL<https://techweb.stryker.com/MedSurg/3002S3/0806/maintenance/patriot/3006-009-102C.pdf>, 227 pages.
Su et al., “Ballistocardiogram Measurement System Using Three Load-Cell Sensors Platform in Chair,” 2009 2nd International Conference on Biomedical Engineering and Informatics, Tianjin, 2009, pp. 1-4 (abstract only).
Talbot et al., “Dynamic Comparison of Current Ballistocardiographic Methods: Part I: Artefacts in the Dynamically Simple Ballistocardiographic Methods,” Circulation. 1955, 12:577-587.
VPG Transducers, “Medical Beds,” retrieved from URL<https://vpgtransducers.com/markets/medical>, accessed Nov. 2020, 3 pages.
Watanabe et al., “Ubiquitous Health Monitoring at Home—Sensing of Human Biosignals on Flooring, on Tatami Mat, in the Bathtub, and in the Lavatory,” in IEEE Sensors Journal, vol. 9, No. 12, Dec. 2009, pp. 1847-1855.
Williams, “This 30-ppm Scale Proves that Analog Designs Aren’t Dead Yet,” Oct. 5, 1976, 4 pages.
International Preliminary Report on Patentability in International Appln. No. PCT/US2023/037254, mailed on May 30, 2025, 17 pages.

* cited by examiner

810a
Bed Data Cloud
Network Interface 1600
Communication Manager 1602
Server Hardware 1604
Server System Software 1606
User Identification 1608
Device Management 1610
Sensor Data 1612
Advanced Sleep Data 1614

2000

USING FORCE SENSORS IN BED SYSTEMS

CROSS-REFERENCE TO RELATED APPLICATIONS

This application claims the benefit of U.S. Provisional Application Ser. No. 63/426,119, filed Nov. 17, 2022. The disclosure of the prior application is considered part of the disclosure of this application, and is incorporated in its entirety into this application.

The present document relates to automation of a consumer device such as an airbed.

BACKGROUND

In general, a bed is a piece of furniture used as a location to sleep or relax. Many modern beds include a soft mattress on a bed frame. The mattress may include springs, foam material, and/or an air chamber to support the weight of one or more occupants.

SUMMARY

Some embodiments described herein include systems and methods related to consumer devices such as an airbed that include one or more force sensors. For example, a bed system can include a mattress, a support platform, and a plurality of legs. The bed system can include a plurality of force sensors that collect signals that are used to determine parameters of one or more users of the bed system.

Some embodiments described herein include a bed system. The bed system includes a support platform and a plurality of legs supporting the support platform. Each leg of the plurality of legs may include: a mount positioned in the leg and connected to an inside surface of the leg, a force sensor connected to the mount, the force sensor configured to sense a force applied to the leg, a foot that extends around the force sensor and the mount and contacts a floor, the foot having deformable portions along a bottom of the foot and a plate that aligns with the force sensor, where the deformable portions are configured to facilitate movement of the plate to compress the force sensor in response to a force applied to the foot along a vertical axis, and a preamplifier connected to the force sensor and positioned above the mount.

Embodiments described herein can include one or more optional features. For example, the deformable portions facilitate vertical movement of the plate responsive to one or more forces applied to the leg. The foot and the mount constrain the force sensor to two degrees of freedom. The two degrees of freedom are vertical motion and rotational motion. The deformable portions extend from a plate portion of the foot and end at an offset distance from an outer edge of the bottom of the foot. A sensing surface of the force sensor is exposed below the mount to facilitate contact between the plate and the force sensor. The foot may include a rubber material that facilitates deformation of the deformable portions. A sensing surface of the force sensor faces towards the plate and a non-sensing surface faces towards the mount. The one or more user parameters include at least one of sleeper weight, biometrics, sleep stage, restlessness, and user presence. Implementations of the described techniques may include hardware, a method or process, or computer software on a computer-accessible medium.

Some embodiments described herein include a bed system. The bed system includes a foundation frame configured to support a mattress, and at least a first leg defining a vertical axis. The first leg may include a leg shaft mounted to the foundation frame and extending downward from the foundation frame for supporting the foundation frame, a leg foot connected to a distal end of the leg shaft, where the leg foot has a foot bottom configured to contact a floor; and a force sensor positioned between the leg shaft and the leg foot, where the leg foot is configured to move with respect to the leg shaft to compress the force sensor when a force is applied to the first leg along the vertical axis.

Embodiments described herein can include one or more optional features. For example, the bed system may include a controller in communication with the force sensor, the controller configured to: receive a plurality of force signals from the force sensor; analyze the plurality of force signals; and generate one or more user parameters. The one or more user parameters include at least one of sleeper weight, biometrics, sleep stage, restlessness, and user presence. The force sensor is constrained to two degrees of freedom.

Some embodiments described herein include a bed system. The bed system also includes a support platform configured for supporting a mattress; and a plurality of legs supporting the support platform, each of the plurality of legs may include: a mount positioned in the leg and connected to an inside surface of the leg; a carrier positioned below the mount and connected to the mount, the carrier and the mount defining a chamber between the mount and the carrier; a force sensor positioned in the chamber, and the chamber constrains the force sensor to two degrees of freedom, the force sensor configured to sense a force applied along a vertical axis of the leg that compresses the force sensor in the chamber; a preamplifier connected to the force sensor and positioned above the mount.

Embodiments described herein can include one or more optional features. For example, the bed system where the two degrees of freedom are vertical motion and rotational motion. The rotational motion is about a vertical axis. A sensing surface of the force sensor is exposed above the carrier to facilitate contact between the mount and the force sensor. A foot is a rubber foot that is positioned between the force sensor and a floor. All the force of the bed system translates through each of the force sensors in each of the legs. Implementations of the described techniques may include hardware, a method or process, or computer software on a computer-accessible medium.

Some embodiments described herein include a bed system. The bed system also includes a support platform configured for supporting a mattress; and a plurality of legs supporting the support platform, each of the plurality of legs may include: a mount positioned in the leg and connected to an inside surface of the leg; a carrier positioned below the mount and connected to the mount, the carrier and the mount defining a chamber between the mount and the carrier; a force sensor positioned in the chamber, and the chamber constrains the force sensor to two degrees of freedom, the force sensor configured to sense a force applied along a vertical axis of the leg that compresses the force sensor in the chamber; a preamplifier positioned in one of the plurality of legs above the mount, the preamplifier connected to each of the force sensors.

Embodiments described herein can include one or more optional features. For example, the bed system where the two degrees of freedom are vertical motion and rotational motion. The rotational motion is about a vertical axis. A sensing surface of the force sensor is exposed below the mount to facilitate contact between the plate and the force sensor. A foot is a rubber foot that is positioned between the force sensor and a floor. All the force of the bed system translates through each of the load cells in each of the legs. Implementations of the described techniques may include hardware, a method or process, or computer software on a computer-accessible medium.

Some embodiments described herein include a bed system. The bed system can include a first left leg including a first load cell connected to a first preamplifier. The bed system also includes a first right leg including a second load cell connected to a second preamplifier. The bed system also includes a second left leg including a third load cell connected to the first preamplifier in the first left leg. The bed system also includes and a second right leg including a fourth load cell connected to the second preamplifier in the first right leg.

Embodiments described herein can include one or more optional features. For example, the bed system may include a foundation frame configured to support a mattress, the first left leg, the first right leg, the second left leg, and the second right leg extending downward from the foundation frame for supporting the foundation frame. The first left leg defines a first left foot cavity positioned at a foot of the first left leg, where the first left foot cavity contains the first load cell and the first preamplifier; the first right leg defines a first right foot cavity positioned at a foot of the first right leg, where the first right foot cavity contains the second load cell and the second preamplifier; the second left leg defines a second left foot cavity positioned at a foot of the second left leg, where the second left foot cavity contains the third load cell; the second right leg defines a second right foot cavity positioned at a foot of the second right leg, where the second right foot cavity contains the fourth load cell. Implementations of the described techniques may include hardware, a method or process, or computer software on a computer-accessible medium.

Some embodiments described herein include a bed system. The bed system also includes a support platform configured for supporting a mattress; and a plurality of legs supporting the support platform, each of the plurality of legs may include: a mount positioned in the leg and connected to an inside surface of the leg; a force sensor connected to the mount, the force sensor configured to sense a force applied along a vertical axis of the leg; a carrier positioned below the mount and the force sensor and connected to the force sensor, the carrier having external walls that extend upwardly from a bottom plate of the carrier, where the external walls of the carrier and a bottom surface of the leg define a gap between the external walls and the bottom surface of the leg; a foot that extends around the carrier and the bottom surface of the leg and contacts a floor.

Embodiments described herein can include one or more optional features. For example, the bed system where the force sensor is constrained to two degrees of freedom. The two degrees of freedom are vertical motion and rotational motion. The rotational motion is about a vertical axis. A foot is a rubber foot that is positioned between the force sensor and a floor. All the force of the bed system translates through each of the load cells in each of the legs. The bed system may include: a controller in communication with the force sensor, the controller configured to: receive a plurality of force signals from the force sensor; analyze the plurality of force signals; and generate one or more user parameters. The one or more user parameters include at least one of sleeper weight, biometrics, sleep stage, restlessness, and user presence. Implementations of the described techniques may include hardware, a method or process, or computer software on a computer-accessible medium. The devices, systems, and techniques described herein may provide one or more of the following advantages. For example, the bed systems described herein provide improved accuracy of force signals from force sensors. The bed systems described herein can restrict the force sensors to two degrees of freedom and reduce or eliminate noise from friction or other forces that would distort the force signals. The individual force sensor signals or combination of force sensor signals can be used to determine user parameters such as sleeper weight, biometrics, sleep stage, restlessness, presence, or position with improved accuracy and precision.

Another advantage of the bed systems described herein includes an integration of force sensors into the legs of the bed system. Legs with integrated force sensors provides for ease of assembly and operation of the bed system. The force sensors and bed legs can be replaced as needed without the need for a technician to support the removal or installation process. Installation of the legs and force sensors is simplified and facilitates improved data collection results by having predictable and accurate force sensor placement.

The details of one or more implementations are set forth in the accompanying drawings and the description below. Other features, aspects, and potential advantages will be apparent from the accompanying description and figures.

DESCRIPTION OF DRAWINGS

Like reference symbols in the various drawings indicate like elements.

DETAILED DESCRIPTION

This disclosure relates to using various sensors within a bed system (such as an airbed or other type of bed), including force sensors connected to or integrated in one or more components of the bed system to measure a variety of sleep parameters. The parameters can be used by a control system to make determinations about an occupant, or user, of the bed. For example, a bed system can include a mattress, a support platform, and a plurality of legs. The bed system can include a plurality of force sensors that collect signals that are used to determine parameters of one or more users of the bed system.

In some aspects, the plurality of force sensors can be integrated in the plurality of legs. For example, each leg includes an integrated force sensor. Each of the plurality of legs can include a preamplifier that is integrated in the leg. In another example, the bed system can include one or more preamplifiers per side of the bed system, and the plurality of force sensors can connect to the preamplifier on the side of the bed system where the respective force sensors are located.

In some aspects, the plurality of force sensors are positioned and constrained in the bed system such that the forces applied on the load cells are aligned to be vertical forces. In some aspects, the force sensors can be constrained to two degrees of freedom to reduce or eliminate signal noise.

Figure 1:
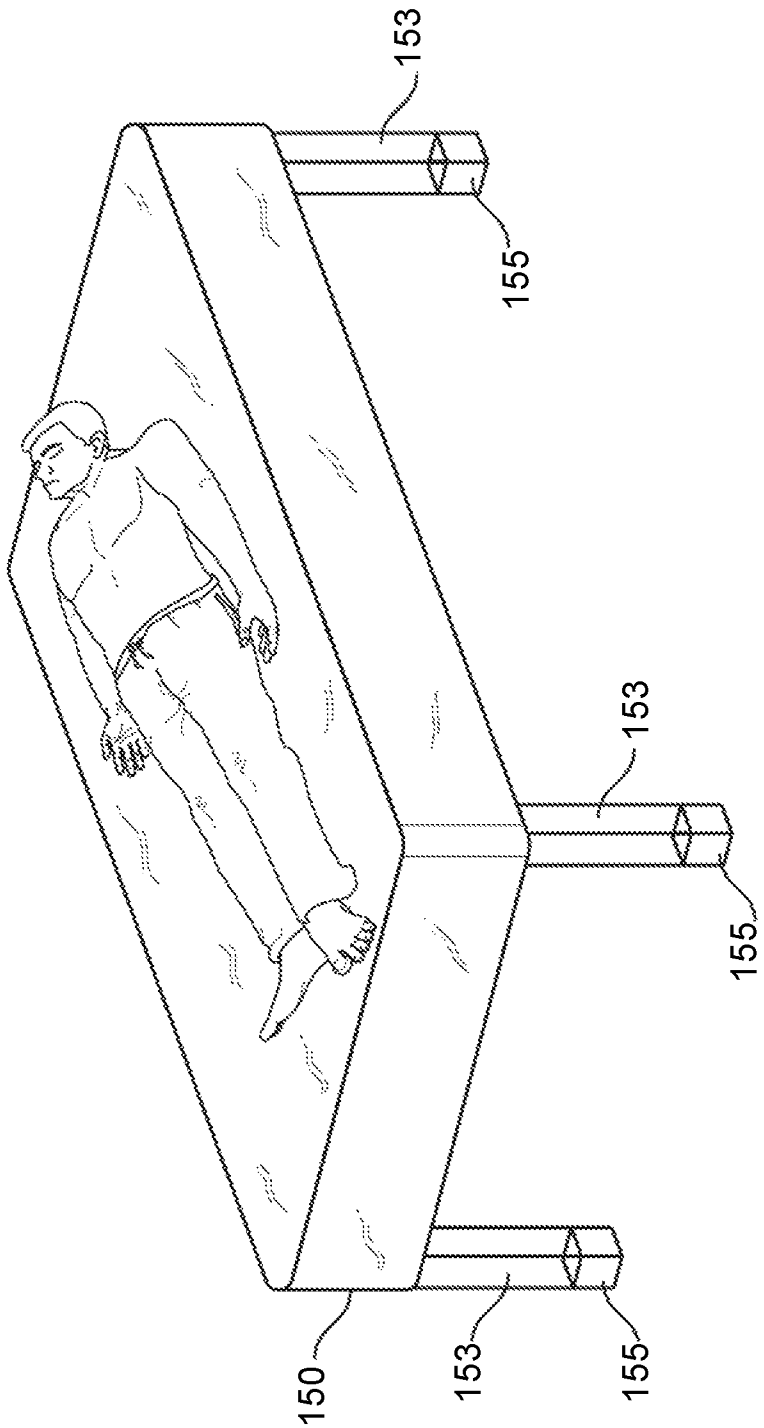
FIG. 1 is a schematic diagram of an example bed with force sensors located at the bottom of the legs of the bed.

FIG. 1 is a schematic diagram of an example bed with force sensors 155 located at the bottom of legs 153 of the bed (e.g., in four, six, eight, or another number of legs). The force sensors 155 may also be located elsewhere on the bed with a similar effect (e.g., between the legs 153 and platform 150). When a strain gauge is used as the force sensors 155, the force sensor(s) 155 can be positioned near the center of the legs 153. The force sensors 155 can be load cells.

Figure 2A:
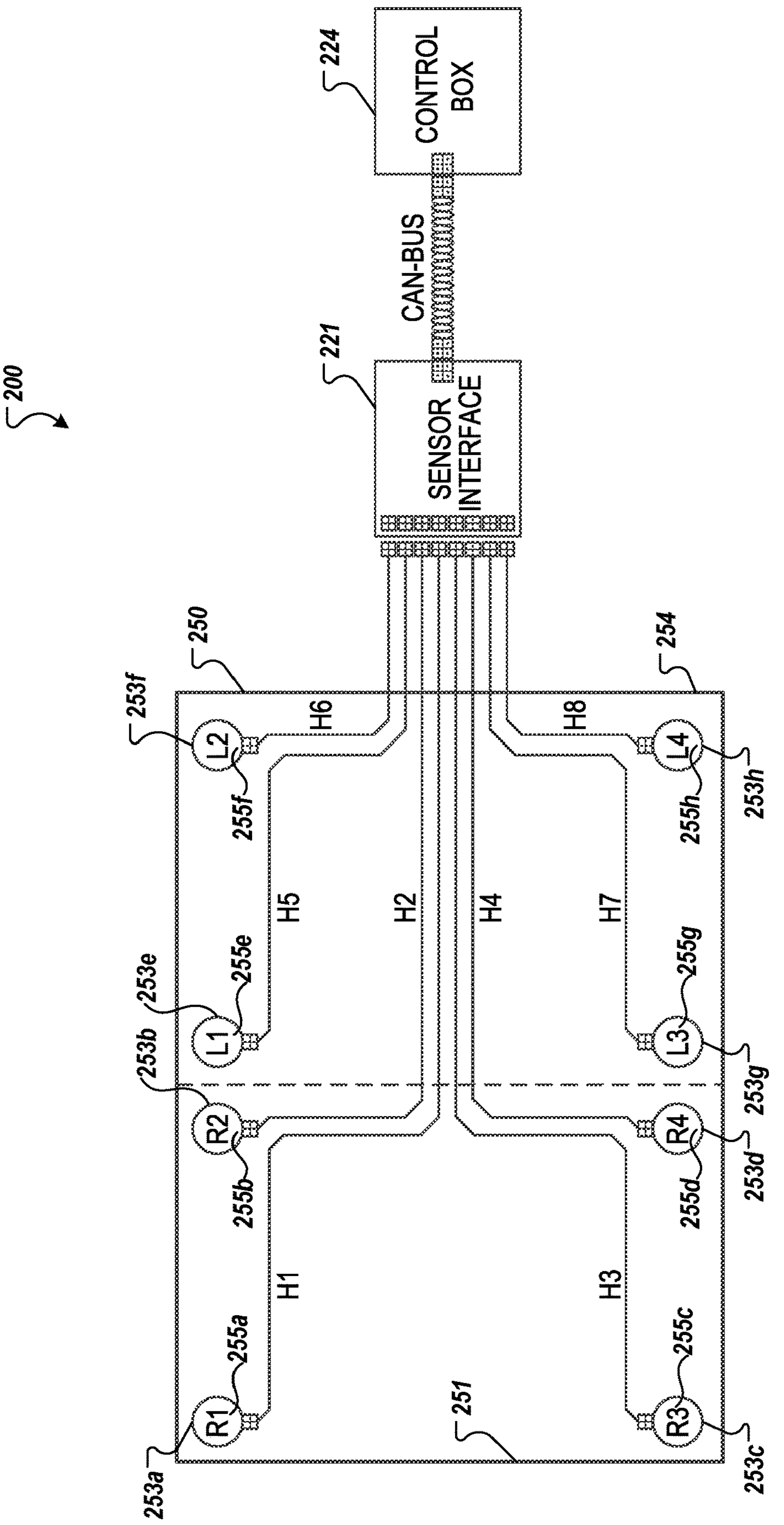
FIG. 2A is a schematic bottom view of an example bed system.

FIG. 2A shows a schematic diagram of a bottom of an example bed system 200. The bed system 200 includes a platform 250 that is configured to support a mattress that can include one or more layers that can include foam layers, and air chambers, among other layers as described in further detail below. The platform 250 is supported on the ground by a plurality of legs 253 that are positioned at various locations around the platform 250 to provide support to the platform 250 and hold the platform 250 off of the ground. In the example shown in FIG. 2, the plurality of legs 253 includes eight legs (253*a*, 253*b*, 253*c*, 253*d*, 253*e*, 253*f*, 253*g*, 253*h*), including four legs (e.g., legs 253*a*, 253*b*, 253*c*, 253*d*) on the right side 251 of the platform 250 and four legs on the left side 254 of the platform 250. Each of the plurality of legs 253 includes a force sensor (255*a*, 255*b*, 255*c*, 255*d*, 255*e*, 255*f*, 255*g*, and 255*h*), connected to or integrated in each of the plurality of legs 253. The plurality of force sensors 255 are connected to a sensor interface 221 that collects the signals from the plurality of force sensors 255 and communicates the signals to a control box 224.

In some aspects, the plurality of force sensors 255 can be a plurality of load cells. For example, the force sensors 255 can be tension, compression, or alternating load cells. The force sensors 255 can be load cells that have various shapes such as washer shaped load cells, beam type load cells, S-shaped load cells, and can type load cells. The force sensors 255 can also include single point load cells and/or multi point load cells. The force sensors 255 can also be a strain gauge load cell, a hydraulic load cell, a pneumatic load cell, a capacitive load cell, and a piezoelectric transducer.

The plurality of force sensors 255 can each be mechanically mounted or integrated into the plurality of legs 253 and measure vertical forces applied to the force sensors 255. Each force sensor 255 provides a scaled electrical output as force(s) are applied to the force sensor 255. The signals from each individual force sensor 255, or the combination of multiple force sensor signals, can be used to determine sleeper weight, biometrics, sleep stage, restlessness, presence, or position. Each force sensor 255 is positioned in the bed system 200 at positions that reduce or eliminate the influence of lateral loads on the load cell, as will be described in detail below. In addition to the plurality of force sensors 255 positioned in the plurality of legs 253, the bed system 200 can include one or more force sensors positioned around the platform 250. For example, the platform The control box 224 can include one or more processors that analyze a force signal detected by one or more of the plurality of force sensors 225 to determine a user's presence, user weight, sleep stage, restlessness, position, heart rate, respiration rate, and/or other vital signs of the user lying or sitting on a mattress on the platform 250. More specifically, when a user lies on the bed system 200 and is positioned over the chamber platform 250, each of the user's heart beats, breaths, and other movements (e.g., hand, arm, leg, foot, or other gross body movements) can create a force on the bed system 200 that is transmitted to the chamber 114A.

Sometimes, the control box 224 can receive additional biometric signals of the user from one or more other sensors or sensor arrays positioned on or otherwise integrated into the bed system 200. For example, one or more sensors can be attached or removably attached to a top surface of the bed system 200 and configured to detect signals such as heart rate, respiration rate, and/or motion. The processors of the control box 224 can combine biometric signals received from the sensors positioned throughout the bed system 200 to generate accurate and more precise information about the user and their sleep quality.

Sometimes, the control box 224 can perform a pattern recognition algorithm or other calculation based on amplified and filtered force signal(s) to determine the user's heart rate and/or respiratory rate. For example, the algorithm or calculation can be based on assumptions that a heartrate portion of the signal has a frequency in a range of 0.5-4.0 Hz and that a respiration rate portion of the signal has a frequency in a range of less than 1 Hz. Sometimes, the control box 124 can use one or more machine learning models to determine the user's health information. The models can be trained using training data that includes training force signals and expected heart rates and/or respiratory rates. Sometimes, the control box 224 can determine user health information by using a lookup table that corresponds to sensed force signals.

The control box 224 can also be configured to determine other characteristics of the user based on the received force signals, such as blood pressure, tossing and turning movements, rolling movements, limb movements, weight, presence or lack of presence of the user, and/or the identity of the user.

For example, the plurality of force sensors 255 can be used to monitor the forces applied to the plurality of legs 253 of the bed system 200. If the user on the bed system 200 is not moving, the force changes at the plurality of force sensors 255 can be relatively minimal, and can be attributable to respiration and/or heartbeat. When the user on the bed system 200 is moving (e.g., tossing and turning, getting in and out of bed), however, the forces at the plurality of force sensors 255 can fluctuate by a much larger amount. The force signals generated by the force sensors 255 and received by the control box 224 can be filtered and indicated as corresponding to motion, heartbeat, or respiration. The processor(s) at the control box 224 can attribute such fluctuations in forces to the user's sleep quality. Such attributions can be determined based on applying one or more machine learning models and/or algorithms to the force signals. For example, if the user shifts and turns a lot during a sleep cycle (for example, in comparison to historic trends of the user's sleep cycles), the processor(s) can determine that the user experienced poor sleep during that particular sleep cycle.

In some implementations, rather than performing the data analysis in the control box 224 with the processor(s), a digital signal processor (DSP) can be provided to analyze the data collected by the plurality of force sensors 255. Alternatively, the collected data can be sent to a cloud-based computing system for remote analysis.

Figure 2C:
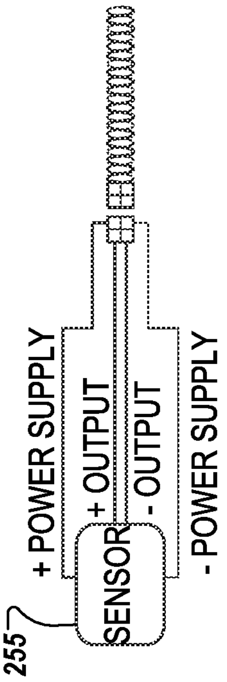
FIG. 2C is a schematic diagram of an example force sensor.
Figure 2B:
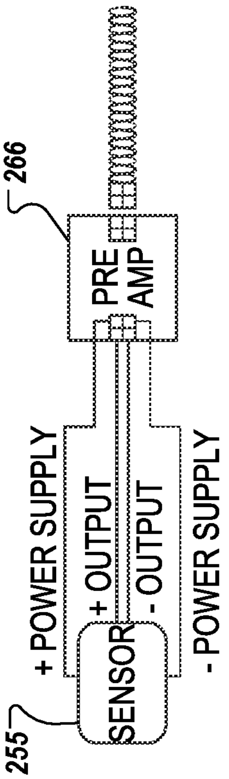
FIG. 2B is a schematic diagram of an example force sensor and preamplifier assembly.

FIG. 2B shows an example of a force sensor 255 and a preamplifier 266 that are integrated into a leg (e.g., the leg 253*a*). Each of the plurality of legs 253 can include a preamplifier (e.g., the preamplifier 266) that is integrated in the leg 253 such that each leg (e.g. legs 253*a*, 253*b*, 253*c*, 253*d*, 253*e*, 253*f*, 253*g*, 253*h*) includes a force sensor (e.g., force sensors 255*a*, 255*b*, 255*c*, 255*d*, 255*e*, 255*f*, 255*g*, 255*h*), and a preamplifier (e.g., preamplifier 266) where the bed system 200 includes an equal number of preamplifiers and force sensors. The preamplifier 266 amplifies the electrical output from the force sensor 255 before the output is sent to the sensor interface 221 and the control box 224.

FIG. 2C shows another example, where the force sensor 255 is integrated into a leg (e.g., the leg 253*a*), and a preamplifier is not integrated into the leg with the force sensor 255. The bed system 200 can include one or more preamplifiers (e.g., the preamplifier 266) per side of the bed system 200, and the plurality of force sensors 255 can connect to the preamplifier on the side of the bed system that the respective force sensors 255 are located.

Figure 3:
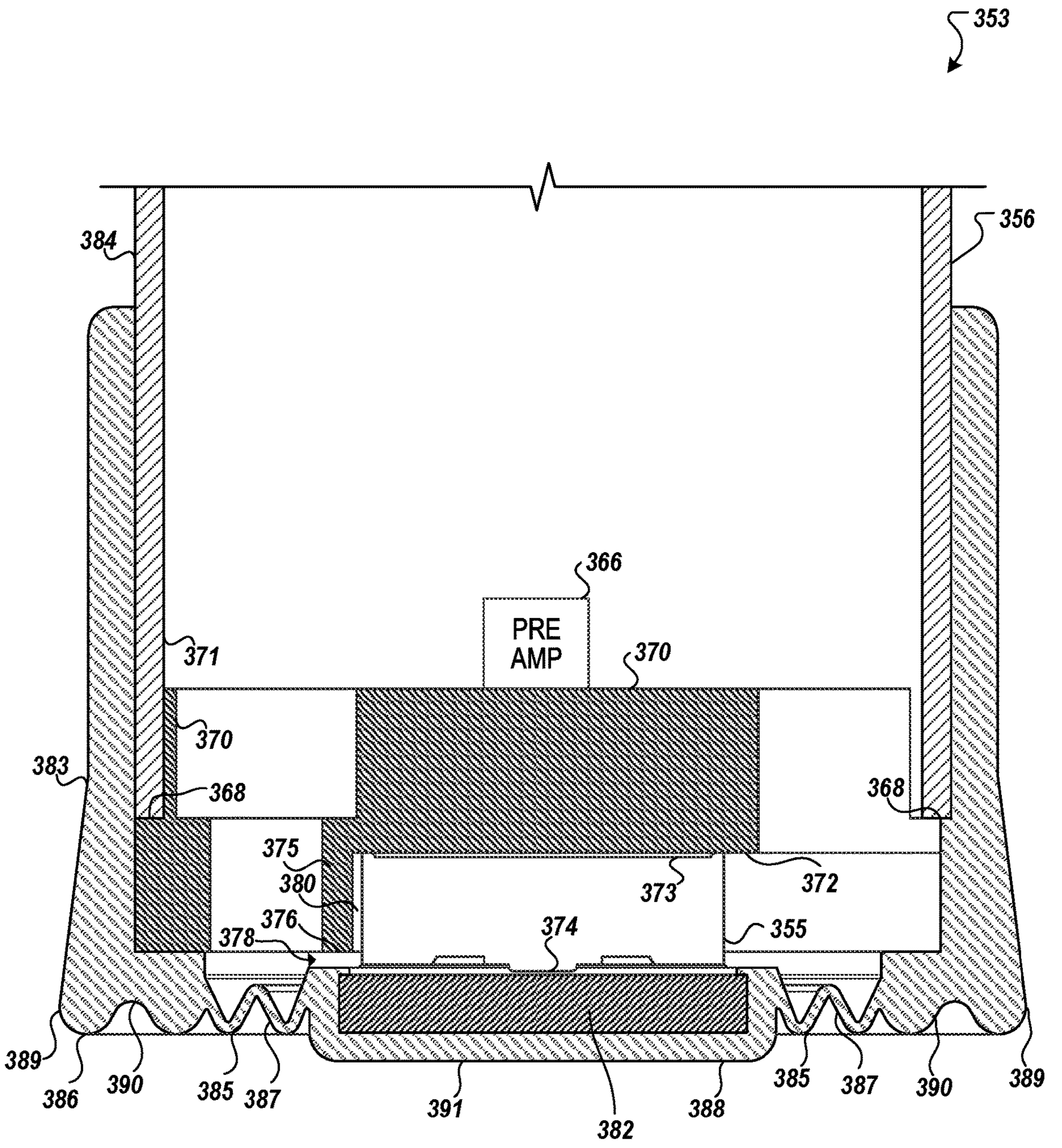
FIG. 3 is a cross-sectional view of a leg of an example bed system.

FIG. 3 shows an example of a leg 353 with a force sensor 355 that can be installed in the bed system described herein. The leg 353 includes a leg wall 356 that can connect to a bed platform (e.g., platform 250), and a plurality of legs 353 each having a force sensor 355 can support the bed platform and operate in a similar manner to the plurality of legs 253 and force sensors 255 described above.

The leg 353 includes a mount 370 positioned in the leg 353 and connected to an inside surface 371 of the leg wall 356. The force sensor 355 is positioned generally below the mount 370 such that the force sensor 355 is between the mount 370 and a floor during operation of the bed system. The mount 370 extends into contact with and connection to the inside surface 371 of the leg wall 356 at or near a bottom end 368 of the leg wall 356. The mount 370 includes one or more protrusions 375 that extend around and define a cavity 380 that is dimensioned to receive the force sensor 355. In some embodiments, the mount 370 can be one or more components to which the force sensor 355 is mounted. In some aspects, the mount 370 and the force sensor 355 are connected to each other along a cavity surface 372 of the mount 370 and along a first surface 373 of the force sensor 355. In other aspects, the force sensor 355 is positioned within the cavity 380 without connection to the mount 370. In some embodiments, the mount 370 can be any suitable structure between the force sensor 355 and the bed platform in order to hold the force sensor 355 with respect to the plate 382 and the foot 383.

The force sensor 355 can be a disc style load cell that senses forces applied to the leg 353. In some aspects, the force sensor 355 can include the first surface 373 and a second surface 374, where the second surface 374 is a button or sensing surface of the disc style load cell that receives the force applied to the force sensor. In operation, the first surface 373 can be positioned above the second surface 374 such that the second surface 374 faces towards a floor while the first surface 373 faces towards the bed system. The second surface 374 protrudes beyond the lower surface 376 of the mount 370 such that there is a gap 378 between the lower surface 376 of the mount 370 and the second surface 374 of the force sensor 355. The second surface 374 of the force sensor 355 is exposed below the lower surface 376 of the mount 370 to facilitate contact between a plate 382 and the second surface 374 of the force sensor 355.

The plate 382 is connected to a foot 383 that extends around a lower portion of the leg 353 and contacts the floor. The foot 383 extends around an outside surface 384 of the leg wall 356, the mount 370, and the force sensor 355 and closes the bottom end of the foot 383. The foot 383 extends along a portion of the outside surface 384 of the leg wall 356. In some aspects, the foot 383 includes a rubber material that facilitates selective deformation of the foot 383 and grip with the floor.

The foot 383 includes one or more deformable portions 385 along a bottom end 386 of the foot 383. The deformable portions 385 can include one or more angled members 387 that are flexible and are configured to bend or deform in response to forces applied to the foot 383. The deformable portions 385 extend from a plate portion 388 of the foot 383 and end at an offset distance from an outer edge 389 of the bottom of the foot. In some aspects, the offset distance is equal to a width of a lateral portion 390 of the foot 383 that extends between the deformable portions 385 and the outer edge 389 of the foot 383.

The plate portion 388 of the foot 383 extends between the deformable portions 385 and houses the plate 382. The plate portion 388 has a floor contact surface 391 that extends lower than the bottom end 386 of the foot 383 in operation. The floor contact surface 391 of the plate portion 388 is a primary contact point between the leg 353 and the floor. The plate portion 388 aligns the plate 382 with the force sensor 355.

The deformable portions 385 facilitate vertical movement of the plate 382 in response to forces applied to the leg 353. The deformable portions 385 are positioned to deform in response to forces applied to the leg 353, the deformation of the deformable portions 385 facilitates vertical translation of the plate portion 388 into contact with the second surface 374 of the force sensor 355. In some aspects, vertical translation of the plate 382 and the plate portion 388 can close the gap 378 between the lower surface 376 of the mount 370 and the second surface 374 of the force sensor 355.

In some aspects, the force sensor 355 is constrained to two degrees of freedom. For example, the force sensor 355 is positioned in the cavity 380 between the mount 370 and the plate 382, and the force sensor 355 can move in a vertical direction in response to forces on the leg 353, and the force sensor 355 can rotate within the cavity. The rotational motion of the force sensor 355 is about a vertical axis that extends through the leg 353. As such, the force sensor 355 is constrained to two degrees of freedom thereby limiting noise in the force signals generated by the force sensor 355.

The force signals generated by the force sensor 355 can be passed through a preamplifier 366 that is positioned in the leg 353. In some aspects, the preamplifier 366 is positioned above the mount 370 in operation. The preamplifier 366 amplifies the electrical output from the force sensor 355 before the output is sent to a sensor interface (e.g., the sensor interface 221) and a control box (e.g., the control box 224). In other aspects, the preamplifier 366 can be positioned outside of the leg 353 or in one leg 353 per side of the bed system such that each leg 353 does not include a preamplifier.

Figure 4:
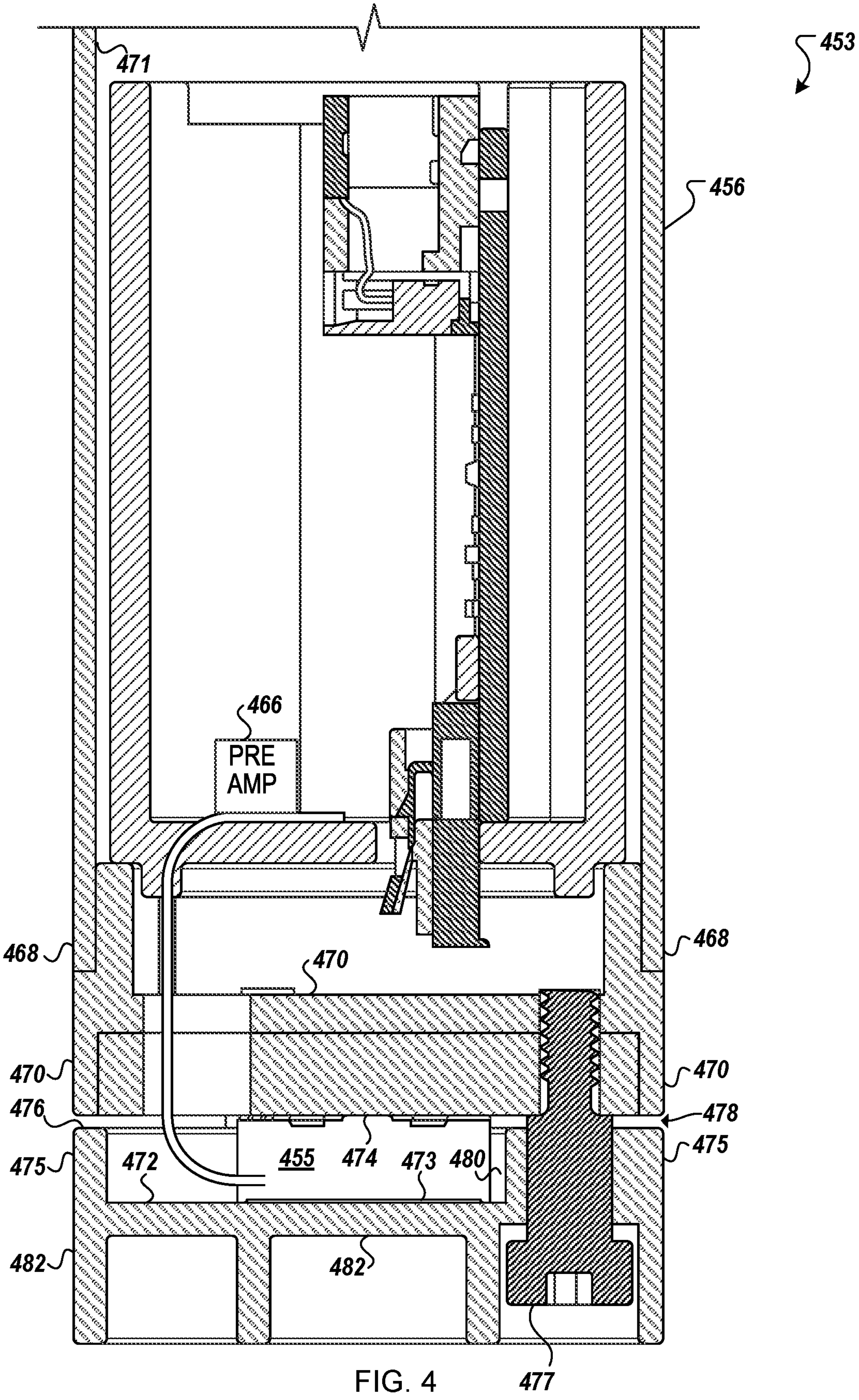
FIG. 4 is a cross-sectional view of a leg of another example bed system.

FIG. 4 shows an example of a leg 453 with a force sensor 455 that can be installed in the bed systems described herein. The leg 453 includes a leg wall 456 that can connect to a bed platform (e.g., platform 250), and a plurality of legs 453 each having a force sensor 455 can support the bed platform and operate in a similar manner to the plurality of legs 253 and force sensors 255 described above.

The leg 453 includes a mount 470 positioned in the leg 453 and connected to an inside surface 471 of the leg wall 456. The force sensor 455 is positioned below the mount 470 such that the force sensor 455 is between the mount 470 and a floor during operation of the bed system. The mount 470 extends into contact with and connection to the inside surface 471 of the leg wall 456 at or near a bottom end 468 of the leg wall 456. The mount 470 includes one or more fastener openings that receive one or more fasteners such as a fastener 477. In some aspects, the fastener 477 can be a shoulder bolt. The fastener 477 can connect the mount 470 to a carrier 482.

The carrier 482 includes one or more protrusions 475 that extend around and define a cavity 480 between the carrier 482 and the mount 470. The cavity 480 is dimensioned to receive the force sensor 455. In some aspects, the carrier 482 and the force sensor 455 are connected to each other along a cavity surface 472 of the carrier 482 and along a first surface 473 of the force sensor 455. In other aspects, the force sensor 455 is positioned within the cavity 480 without connection to the mount 470 or the carrier 482.

In some aspects, the force sensor 455 can be a disc style load cell that senses forces applied to the leg 453. The force sensor 455 includes the first surface 473 and a second surface 474. In operation, the first surface 473 is positioned below the second surface 474 such that the second surface 474 faces towards the bed system while the first surface 473 faces towards a floor. The second surface 474 protrudes beyond an upper surface 476 of the carrier 482 such that there is a gap 478 between the upper surface 476 of the carrier 482 and the second surface 474 of the force sensor 455. The second surface 474 of the force sensor 455 is exposed above the upper surface 476 of the carrier 482 to facilitate contact between the mount 470 and the second surface 474 of the force sensor 455.

In some aspects, the force sensor 455 is constrained to two degrees of freedom. For example, the force sensor 455 is positioned in the cavity 480 between the mount 470 and the carrier 482, and the force sensor 455 can move in a vertical direction in response to forces on the leg 453, and the force sensor 455 can rotate within the cavity. The rotational motion of the force sensor 455 is about a vertical axis that extends through the leg 453. As such, the force sensor 455 is constrained to two degrees of freedom thereby limiting noise in the force signals generated by the force sensor 455.

The force signals generated by the force sensor 455 can be passed through a preamplifier 466 that is positioned in the leg 453. In some aspects, the preamplifier 466 is positioned above the mount 470 in operation. The preamplifier 466 amplifies the electrical output from the force sensor 455 before the output is sent to a sensor interface (e.g., the sensor interface 221) and a control box (e.g., the control box 224). In other aspects, the preamplifier 466 can be positioned outside of the leg 453 or in one leg 453 per side of the bed system such that some versions of the leg 453 do not include a preamplifier.

Figure 5:
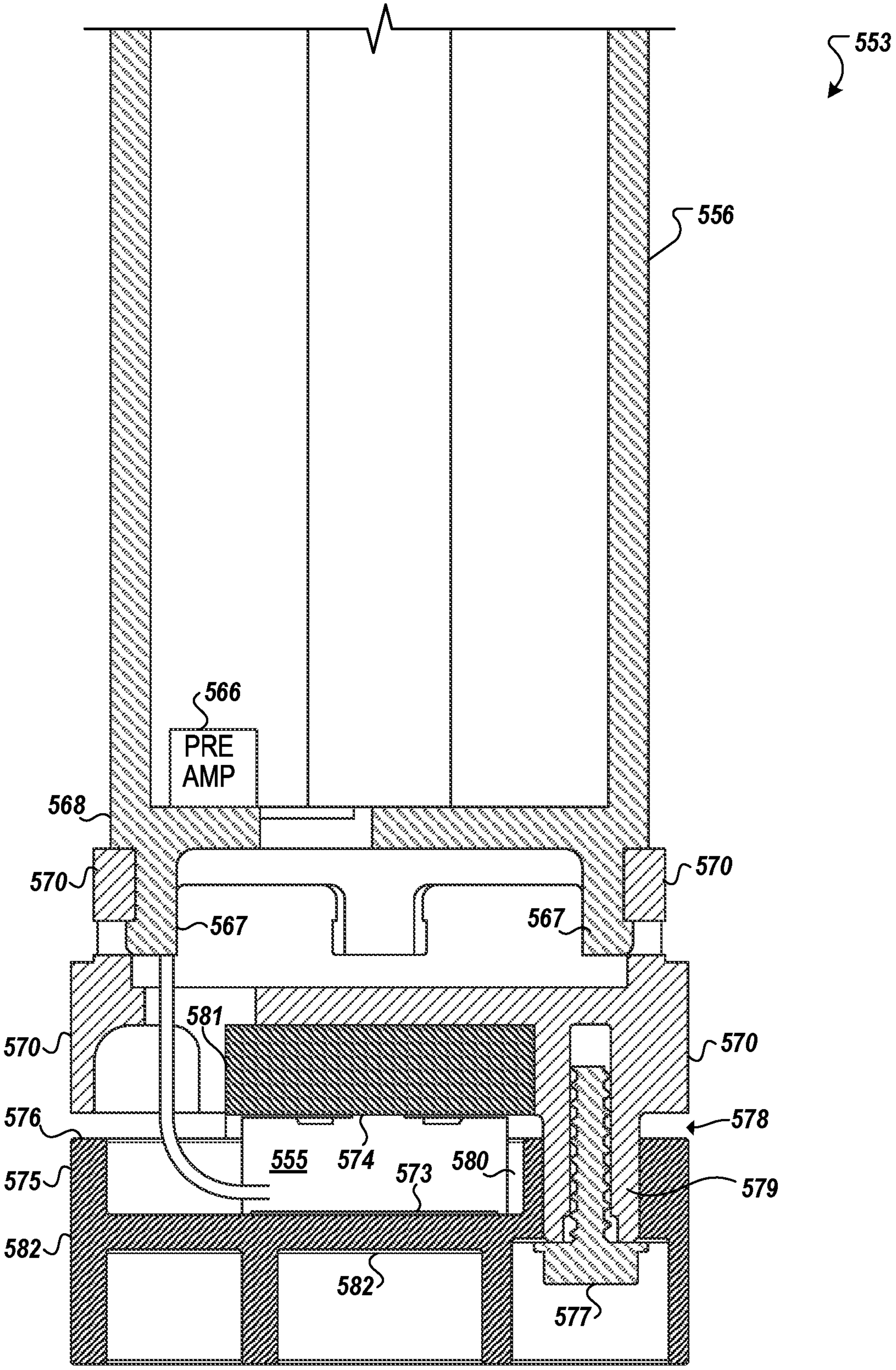
FIG. 5 is a cross-sectional view of a leg of another example bed system.

FIG. 5 shows another example of a leg 553 with a force sensor 555 that can be installed in the bed systems described herein. The leg 553 includes a leg wall 556 that can connect to a bed platform (e.g., platform 250), and a plurality of legs 553 each having a force sensor 555 can support the bed platform and operate in a similar manner to the plurality of legs 253 and force sensors 255 described above (see FIGS. 2A-2C). The leg 553 can share some features with the leg 453 (shown in FIG. 4). For example, the force sensor 555 can be the same or similar to the force sensor 455 (shown in FIG. 4), and can include a first surface 573 and a second surface 574 arranged in the same or similar orientation as the force sensor 455. The leg 553 can also include a mount 570 and a carrier 582 that define a cavity 580 in a similar manner to the mount 470, carrier 482, and cavity 480 of the leg 453 (shown in FIG. 4). The leg 553 can also include a preamplifier 566 that operates in a similar manner to the preamplifier 466 (shown in FIG. 4).

The leg 553 can differ from the leg 453 in some ways. For example, the mount 570 is connected to a leg bracket 567 that is positioned at the bottom end 568 of the leg 553. The mount 570 seats into the leg bracket 567 and extends from the leg bracket 567 into connection with the carrier 582. The mount 570 can connect to or include a plate 581 that aligns with the force sensor 555. The plate 581 is positioned between the mount 570 and the force sensor 555, and the second surface 574 of the force sensor 555 faces in a direction towards the plate 581. The force sensor 555 is positioned below the mount 570 such that the force sensor 555 is between the mount 570 and a floor during operation of the bed system. The second surface 574 protrudes beyond an upper surface 576 of the carrier 582 such that there is a gap 578 between the upper surface 576 of the carrier 582 and the second surface 574 of the force sensor 555. The second surface 574 of the force sensor 555 is exposed above the upper surface 576 of the carrier 582 to facilitate contact between the plate 581 and the second surface 574 of the force sensor 555.

The mount 570 includes one or more fastener protrusions 579 that extend in a downward direction. The one or more fastener protrusions 579 have one or more fastener openings that receive one or more fasteners such as a fastener 577. The one or more fastener protrusions 579 can extend into the carrier 582 to facilitate connection between the mount 570 and the carrier 582 via the fastener 577. In some aspects, the fastener 577 can be a screw such as a plastic screw, a metal screw, or other screws.

The carrier 582 includes one or more protrusions 575 that extend around and define the cavity 580 between the carrier 582 and the mount 570. The cavity 580 is dimensioned to receive the force sensor 555. In some aspects, the carrier 582 and the force sensor 555 are connected to each other along a cavity surface 572 of the carrier 582 and along the first surface 573 of the force sensor 555. In other aspects, the force sensor 555 is positioned within the cavity 580 without connection to the mount 570 or the carrier 582.

The legs 253, 353, 453, and 553 can be implemented into the bed system (e.g., bed system 200). For example, the bed system 200 can include a plurality of legs 353, a plurality of legs 453, or a plurality of legs 553 in place of legs 253*a*, 253*b*, 253*c*, 253*d*, 253*e*, 253*f*, 253*g*, 253*h*. The plurality of legs facilitates an ease of installation because the one or more force sensors are integrated into the leg, thereby simplifying the installation process and facilitating improved data collection results by having predictable and accurate force sensor placement. Additionally, the load cell or leg assembly can be disconnected and replaced individually.

Example Bed Hardware

Figure 6:
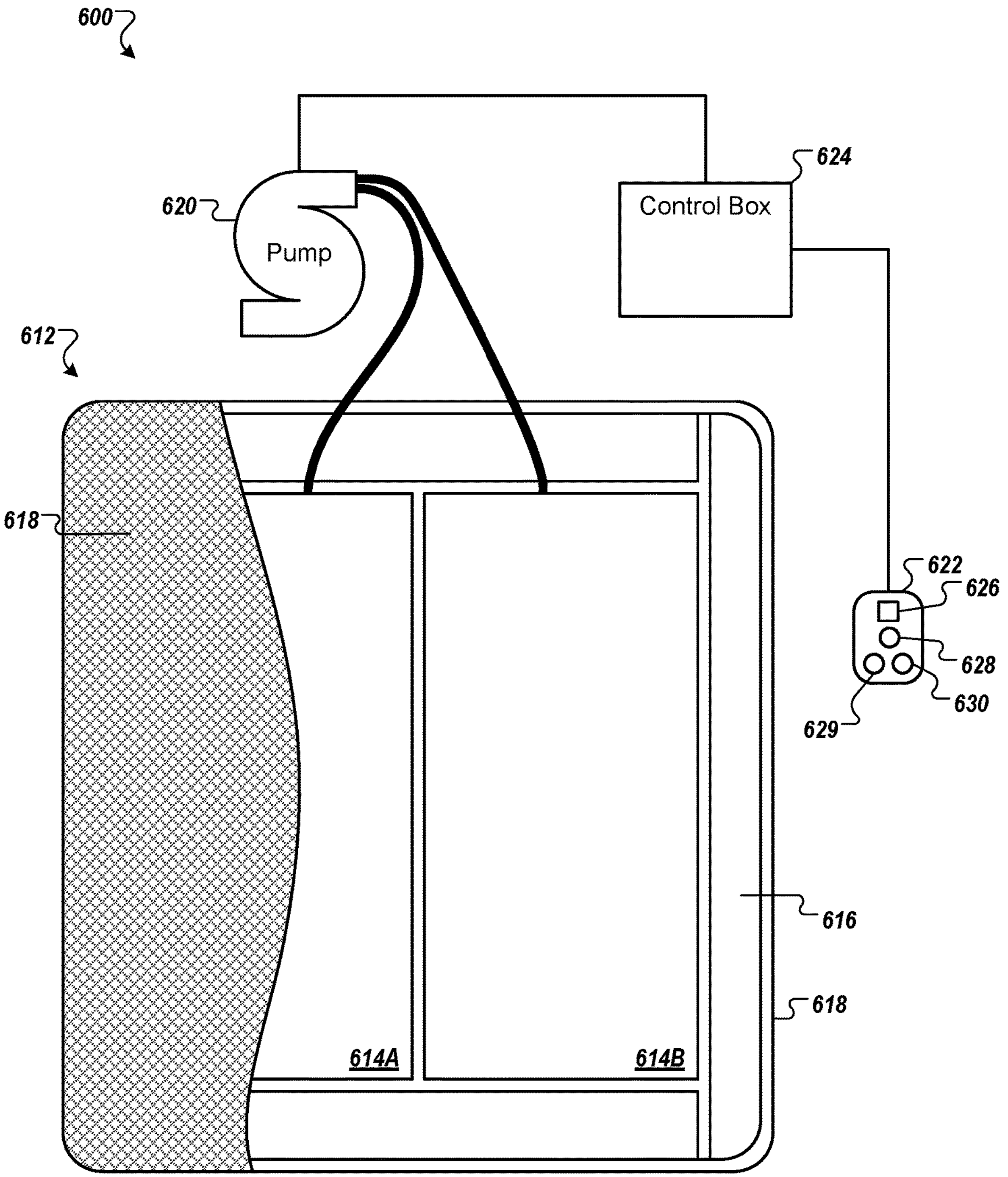
FIG. 6 shows an example air bed system.
Figure 7:
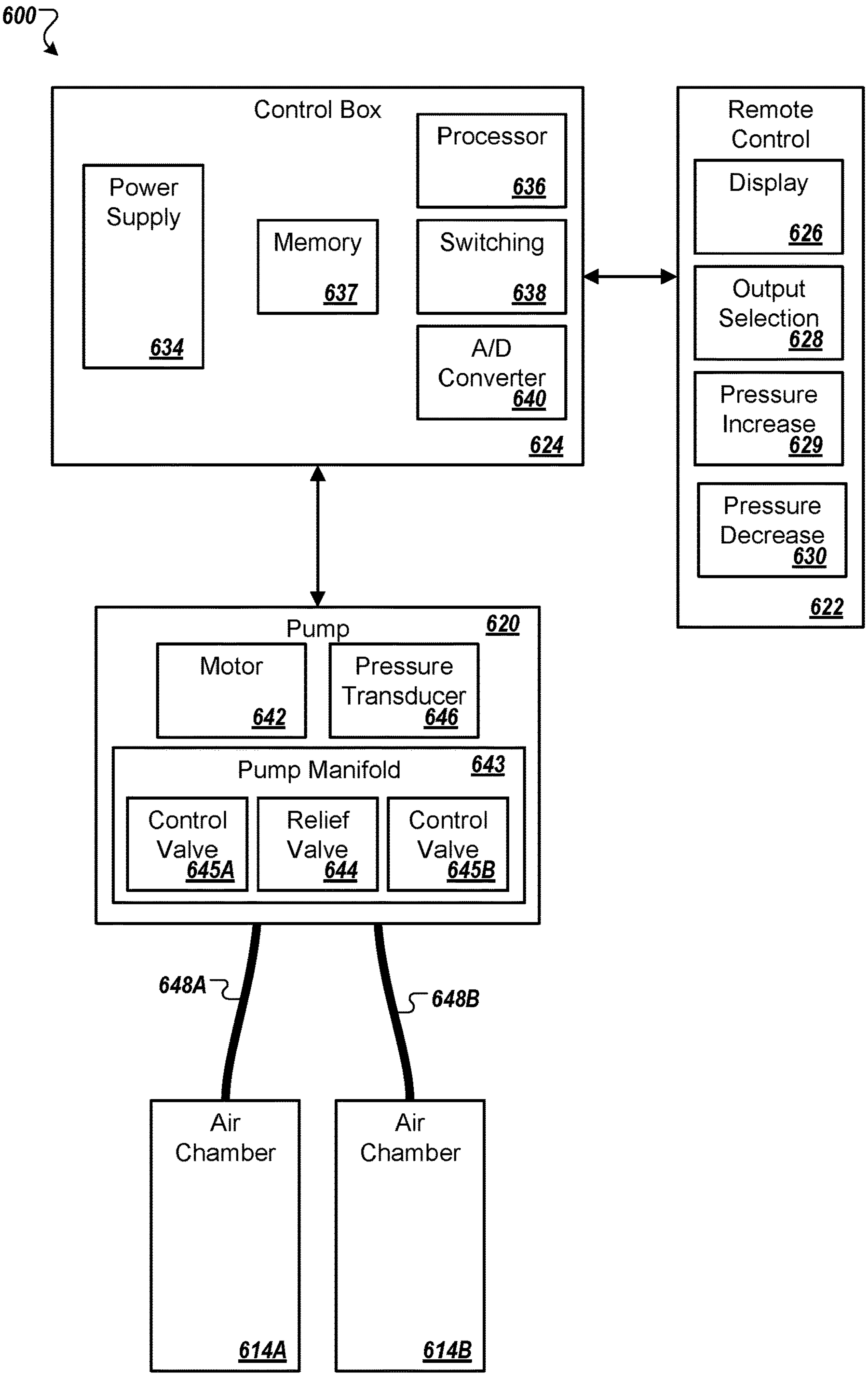
FIG. 7 is a block diagram of an example of various components of an air bed system.

FIG. 6 shows an example air bed system 600 that includes a bed 612. In some embodiments, the legs and force sensors described above can be used with some, all, or none of the features described herein for the air bed system 600. The bed 612 can be a mattress that includes at least one air chamber 614 surrounded by a resilient border 616 and encapsulated by bed ticking 618. The resilient border 616 can comprise any suitable material, such as foam. In some embodiments, the resilient border 616 can combine with a top layer or layers of foam (not shown in FIG. 6) to form an upside down foam tub. In other embodiments, mattress structure can be varied as suitable for the application.

As illustrated in FIG. 6, the bed 612 can be a two chamber design having first and second fluid chambers, such as a first air chamber 614A and a second air chamber 614B. Sometimes, the bed 612 can include chambers for use with fluids other than air that are suitable for the application. For example, the fluids can include liquid. In some embodiments, such as single beds or kids' beds, the bed 612 can include a single air chamber 614A or 614B or multiple air chambers 614A and 614B. Although not depicted, sometimes, the bed 612 can include additional air chambers.

The first and second air chambers 614A and 614B can be in fluid communication with a pump 620. The pump 620 can be in electrical communication with a remote control 622 via control box 624. The control box 624 can include a wired or wireless communications interface for communicating with one or more devices, including the remote control 622. The control box 624 can be configured to operate the pump 620 to cause increases and decreases in the fluid pressure of the first and second air chambers 614A and 614B based upon commands input by a user using the remote control 622. In some implementations, the control box 624 is integrated into a housing of the pump 620. Moreover, sometimes, the pump 620 can be in wireless communication (e.g., via a home network, WIFI, BLUETOOTH, or other wireless network) with a mobile device via the control box 624. The mobile device can include but is not limited to the user's smartphone, cell phone, laptop, tablet, computer, wearable device, home automation device, or other computing device. A mobile application can be presented at the mobile device and provide functionality for the user to control the bed 612 and view information about the bed 612. The user can input commands in the mobile application presented at the mobile device. The inputted commands can be transmitted to the control box 624, which can operate the pump 620 based upon the commands.

The remote control 622 can include a display 626, an output selecting mechanism 628, a pressure increase button 629, and a pressure decrease button 630. The remote control 622 can include one or more additional output selecting mechanisms and/or buttons. The display 626 can present information to the user about settings of the bed 612. For example, the display 626 can present pressure settings of both the first and second air chambers 614A and 614B or one of the first and second air chambers 614A and 614B. Sometimes, the display 626 can be a touch screen, and can receive input from the user indicating one or more commands to control pressure in the first and second air chambers 614A and 614B and/or other settings of the bed 612.

The output selecting mechanism 628 can allow the user to switch air flow generated by the pump 620 between the first and second air chambers 614A and 614B, thus enabling control of multiple air chambers with a single remote control 622 and a single pump 620. For example, the output selecting mechanism 628 can by a physical control (e.g., switch or button) or an input control presented on the display 626. Alternatively, separate remote control units can be provided for each air chamber 614A and 614B and can each include the ability to control multiple air chambers. Pressure increase and decrease buttons 629 and 630 can allow the user to increase or decrease the pressure, respectively, in the air chamber selected with the output selecting mechanism 628. Adjusting the pressure within the selected air chamber can cause a corresponding adjustment to the firmness of the respective air chamber. In some embodiments, the remote control 622 can be omitted or modified as appropriate for an application.

FIG. 2 is a block diagram of an example of various components of an air bed system. These components can be used in the example air bed system 600. The control box 624 can include a power supply 634, a processor 636, a memory 637, a switching mechanism 638, and an analog to digital (A/D) converter 640. The switching mechanism 638 can be, for example, a relay or a solid state switch. In some implementations, the switching mechanism 638 can be located in the pump 620 rather than the control box 624. The pump 620 and the remote control 622 can be in two-way communication with the control box 624. The pump 620 includes a motor 642, a pump manifold 643, a relief valve 644, a first control valve 645A, a second control valve 645B, and a pressure transducer 646. The pump 620 is fluidly connected with the first air chamber 614A and the second air chamber 614B via a first tube 648A and a second tube 648B, respectively. The first and second control valves 645A and 645B can be controlled by switching mechanism 638, and are operable to regulate the flow of fluid between the pump 620 and first and second air chambers 614A and 614B, respectively.

In some implementations, the pump 620 and the control box 624 can be provided and packaged as a single unit. In some implementations, the pump 620 and the control box 624 can be provided as physically separate units. The control box 624, the pump 620, or both can be integrated within or otherwise contained within a bed frame, foundation, or bed support structure that supports the bed 612. Sometimes, the control box 624, the pump 620, or both can be located outside of a bed frame, foundation, or bed support structure (as shown in the example in FIG. 6).

The air bed system 600 in FIG. 2 includes the two air chambers 614A and 614B and the single pump 620 of the bed 612 depicted in FIG. 6. However, other implementations can include an air bed system having two or more air chambers and one or more pumps incorporated into the air bed system to control the air chambers. For example, a separate pump can be associated with each air chamber. As another example, a pump can be associated with multiple chambers. A first pump can be associated with air chambers that extend longitudinally from a left side to a midpoint of the air bed system 600 and a second pump can be associated with air chambers that extend longitudinally from a right side to the midpoint of the air bed system 600. Separate pumps can allow each air chamber to be inflated or deflated independently and/or simultaneously. Additional pressure transducers can also be incorporated into the air bed system 600 such that a separate pressure transducer can be associated with each air chamber.

As an illustrative example, in use, the processor 636 can send a decrease pressure command to one of air chambers 614A or 614B, and the switching mechanism 638 can convert the low voltage command signals sent by the processor 636 to higher operating voltages sufficient to operate the relief valve 644 of the pump 620 and open the respective control valve 645A or 645B. Opening the relief valve 644 can allow air to escape from the air chamber 614A or 614B through the respective air tube 648A or 648B. During deflation, the pressure transducer 646 can send pressure readings to the processor 636 via the A/D converter 640. The A/D converter 640 can receive analog information from pressure transducer 646 and can convert the analog information to digital information useable by the processor 636. The processor 636 can send the digital signal to the remote control 622 to update the display 626 to convey the pressure information to the user. The processor 636 can also send the digital signal to other devices in wired or wireless communication with the air bed system, including but not limited to mobile devices described herein. The user can then view pressure information associated with the air bed system at their device instead of at, or in addition to, the remote control 622.

As another example, the processor 636 can send an increase pressure command. The pump motor 642 can be energized in response to the increase pressure command and send air to the designated one of the air chambers 614A or 614B through the air tube 648A or 648B via electronically operating the corresponding valve 645A or 645B. While air is being delivered to the designated air chamber 614A or 614B to increase the chamber firmness, the pressure transducer 646 can sense pressure within the pump manifold 643. The pressure transducer 646 can send pressure readings to the processor 636 via the A/D converter 640. The processor 636 can use the information received from the A/D converter 640 to determine the difference between the actual pressure in air chamber 614A or 614B and the desired pressure. The processor 636 can send the digital signal to the remote control 622 to update display 626.

Generally speaking, during an inflation or deflation process, the pressure sensed within the pump manifold 643 can provide an approximation of the actual pressure within the respective air chamber that is in fluid communication with the pump manifold 643. An example method includes turning off the pump 620, allowing the pressure within the air chamber 614A or 614B and the pump manifold 643 to equalize, then sensing the pressure within the pump manifold 643 with the pressure transducer 646. Providing a sufficient amount of time to allow the pressures within the pump manifold 643 and chamber 614A or 614B to equalize can result in pressure readings that are accurate approximations of actual pressure within air chamber 614A or 614B. In some implementations, the pressure of the air chambers 614A and/or 614B can be continuously monitored using multiple pressure sensors (not shown). The pressure sensors can be positioned within the air chambers. The pressure sensors can also be fluidly connected to the air chambers, such as along the air tubes 648A and 648B.

In some implementations, information collected by the pressure transducer 646 can be analyzed to determine various states of a user laying on the bed 612. For example, the processor 636 can use information collected by the pressure transducer 646 to determine a heartrate or a respiration rate for the user. As an illustrative example, the user can be laying on a side of the bed 612 that includes the chamber 614A. The pressure transducer 646 can monitor fluctuations in pressure of the chamber 614A, and this information can be used to determine the user's heartrate and/or respiration rate. As another example, additional processing can be performed using the collected data to determine a sleep state of the user (e.g., awake, light sleep, deep sleep). For example, the processor 636 can determine when the user falls asleep and, while asleep, the various sleep states (e.g., sleep stages) of the user. Based on the determined heartrate, respiration rate, and/or sleep states of the user, the processor 636 can determine information about the user's sleep quality. The processor 636 can, for example, determine how well the user slept during a particular sleep cycle. The processor 636 can also determine user sleep cycle trends. Accordingly, the processor 636 can generate recommendations to improve the user's sleep quality and overall sleep cycle. Information that is determined about the user's sleep cycle (e.g., heartrate, respiration rate, sleep states, sleep quality, recommendations to improve sleep quality, etc.) can be transmitted to the user's mobile device and presented in a mobile application, as described above.

Additional information associated with the user of the air bed system 600 that can be determined using information collected by the pressure transducer 646 includes user motion, presence on a surface of the bed 612, weight, heart arrhythmia, snoring, partner snore, and apnea. One or more other health conditions of the user can also be determined based on the information collected by the pressure transducer 646. Taking user presence detection for example, the pressure transducer 646 can be used to detect the user's presence on the bed 612, e.g., via a gross pressure change determination and/or via one or more of a respiration rate signal, heartrate signal, and/or other biometric signals. Detection of the user's presence can be beneficial to determine, by the processor 636, adjustment(s) to make to settings of the bed 612 (e.g., adjusting a firmness when the user is present to a user-preferred firmness setting) and/or peripheral devices (e.g., turning off lights when the user is present, activating a heating or cooling system, etc.).

For example, a simple pressure detection process can identify an increase in pressure as an indication that the user is present. As another example, the processor 636 can determine that the user is present if the detected pressure increases above a specified threshold (so as to indicate that a person or other object above a certain weight is positioned on the bed 612). As yet another example, the processor 636 can identify an increase in pressure in combination with detected slight, rhythmic fluctuations in pressure as corresponding to the user being present. The presence of rhythmic fluctuations can be identified as being caused by respiration or heart rhythm (or both) of the user. The detection of respiration or a heartbeat can distinguish between the user being present on the bed and another object (e.g., a suitcase, a pet, a pillow, etc.) being placed thereon.

In some implementations, pressure fluctuations can be measured at the pump 620. For example, one or more pressure sensors can be located within one or more internal cavities of the pump 620 to detect pressure fluctuations within the pump 620. The fluctuations detected at the pump 620 can indicate pressure fluctuations in the chambers 614A and/or 614B. One or more sensors located at the pump 620 can be in fluid communication with the chambers 614A and/or 614B, and the sensors can be operative to determine pressure within the chambers 614A and/or 614B. The control box 624 can be configured to determine at least one vital sign (e.g., heartrate, respiratory rate) based on the pressure within the chamber 614A or the chamber 614B.

The control box 624 can also analyze a pressure signal detected by one or more pressure sensors to determine a heartrate, respiration rate, and/or other vital signs of the user lying or sitting on the chamber 614A and/or 614B. More specifically, when a user lies on the bed 612 and is positioned over the chamber 614A, each of the user's heart beats, breaths, and other movements (e.g., hand, arm, leg, foot, or other gross body movements) can create a force on the bed 612 that is transmitted to the chamber 614A. As a result of this force input, a wave can propagate through the chamber 614A and into the pump 620. A pressure sensor located at the pump 620 can detect the wave, and thus the pressure signal outputted by the sensor can indicate a heartrate, respiratory rate, or other information regarding the user.

With regard to sleep state, the air bed system 600 can determine the user's sleep state by using various biometric signals such as heartrate, respiration, and/or movement of the user. While the user is sleeping, the processor 636 can receive one or more of the user's biometric signals (e.g., heartrate, respiration, motion, etc.) and can determine the user's present sleep state based on the received biometric signals. In some implementations, signals indicating fluctuations in pressure in one or both of the chambers 614A and 614B can be amplified and/or filtered to allow for more precise detection of heartrate and respiratory rate.

Sometimes, the processor 636 can receive additional biometric signals of the user from one or more other sensors or sensor arrays positioned on or otherwise integrated into the air bed system 600. For example, one or more sensors can be attached or removably attached to a top surface of the air bed system 600 and configured to detect signals such as heartrate, respiration rate, and/or motion. The processor 636 can combine biometric signals received from pressure sensors located at the pump 620, the pressure transducer 646, and/or the sensors positioned throughout the air bed system 600 to generate accurate and more precise information about the user and their sleep quality.

Sometimes, the control box 624 can perform a pattern recognition algorithm or other calculation based on the amplified and filtered pressure signal(s) to determine the user's heartrate and/or respiratory rate. For example, the algorithm or calculation can be based on assumptions that a heartrate portion of the signal has a frequency in a range of 0.5-4.0 Hz and that a respiration rate portion of the signal has a frequency in a range of less than 1 Hz. Sometimes, the control box 624 can use one or more machine learning models to determine the user's health information. The models can be trained using training data that includes training pressure signals and expected heartrates and/or respiratory rates. Sometimes, the control box 624 can determine user health information by using a lookup table that corresponds to sensed pressure signals.

The control box 624 can also be configured to determine other characteristics of the user based on the received pressure signal, such as blood pressure, tossing and turning movements, rolling movements, limb movements, weight, presence or lack of presence of the user, and/or the identity of the user.

For example, the pressure transducer 646 can be used to monitor the air pressure in the chambers 614A and 614B of the bed 612. If the user on the bed 612 is not moving, the air pressure changes in the air chamber 614A or 614B can be relatively minimal, and can be attributable to respiration and/or heartbeat. When the user on the bed 612 is moving, however, the air pressure in the mattress can fluctuate by a much larger amount. The pressure signals generated by the pressure transducer 646 and received by the processor 636 can be filtered and indicated as corresponding to motion, heartbeat, or respiration. The processor 636 can attribute such fluctuations in air pressure to the user's sleep quality. Such attributions can be determined based on applying one or more machine learning models and/or algorithms to the pressure signals. For example, if the user shifts and turns a lot during a sleep cycle (for example, in comparison to historic trends of the user's sleep cycles), the processor 636 can determine that the user experienced poor sleep during that particular sleep cycle.

In some implementations, rather than performing the data analysis in the control box 624 with the processor 636, a digital signal processor (DSP) can be provided to analyze the data collected by the pressure transducer 646. Alternatively, the collected data can be sent to a cloud-based computing system for remote analysis.

In some implementations, the example air bed system 600 further includes a temperature controller configured to increase, decrease, or maintain a temperature of the bed 612, for example for the comfort of the user. For example, a pad (e.g., mat, layer, etc.) can be placed on top of or be part of the bed 612, or can be placed on top of or be part of one or both of the chambers 614A and 614B. Air can be pushed through the pad and vented to cool off the user on the bed 612. Additionally or alternatively, the pad can include a heating element used to keep the user warm. In some implementations, the temperature controller can receive temperature readings from the pad. The temperature controller can determine whether the temperature readings are less than or greater than some threshold range and/or value. Based on this determination, the temperature controller can actuate components to push air through the pad to cool off the user or active the heating element. In some implementations, separate pads are used for different sides of the bed 612 (e.g., corresponding to the locations of the chambers 614A and 614B) to provide for differing temperature control for the different sides of the bed 612. Each pad can be selectively controlled by the temperature controller to provide cooling or heating preferred by each user on the different sides of the bed 612. For example, a first user on a left side of the bed 612 can prefer to have their side of the bed 612 cooled during the night while a second user on a right side of the bed 612 can prefer to have their side of the bed 612 warmed during the night.

In some implementations, the user of the air bed system 600 can use an input device, such as the remote control 622 or a mobile device as described above, to input a desired temperature for a surface of the bed 612 (or for a portion of the surface of the bed 612, for example at a foot region, a lumbar or waist region, a shoulder region, and/or a head region of the bed 612). The desired temperature can be encapsulated in a command data structure that includes the desired temperature and also identifies the temperature controller as the desired component to be controlled. The command data structure can then be transmitted via Bluetooth or another suitable communication protocol (e.g., WIFI, a local network, etc.) to the processor 636. In various examples, the command data structure is encrypted before being transmitted. The temperature controller can then configure its elements to increase or decrease the temperature of the pad depending on the temperature input provided at the remote control 622 by the user.

In some implementations, data can be transmitted from a component back to the processor 636 or to one or more display devices, such as the display 626 of the remote controller 622. For example, the current temperature as determined by a sensor element of a temperature controller, the pressure of the bed, the current position of the foundation or other information can be transmitted to control box 624. The control box 624 can transmit this information to the remote control 622 to be displayed to the user (e.g., on the display 626). As described above, the control box 624 can also transmit the received information to a mobile device to be displayed in a mobile application or other graphical user interface (GUI) to the user.

In some implementations, the example air bed system 600 further includes an adjustable foundation and an articulation controller configured to adjust the position of the bed 612 by adjusting the adjustable foundation supporting the bed. For example, the articulation controller can adjust the bed 612 from a flat position to a position in which a head portion of a mattress of the bed is inclined upward (e.g., to facilitate a user sitting up in bed and/or watching television). The bed 612 can also include multiple separately articulable sections. As an illustrative example, the bed 612 can include one or more of a head portion, a lumbar/waist portion, a leg portion, and/or a foot portion, all of which can be separately articulable. As another example, portions of the bed 612 corresponding to the locations of the chambers 614A and 614B can be articulated independently from each other, to allow one user positioned on the bed 612 surface to rest in a first position (e.g., a flat position or other desired position) while a second user rests in a second position (e.g., a reclining position with the head raised at an angle from the waist or another desired position). Separate positions can also be set for two different beds (e.g., two twin beds placed next to each other). The foundation of the bed 612 can include more than one zone that can be independently adjusted.

Sometimes, the bed 612 can be adjusted to one or more user-defined positions based on user input and/or user preferences. For example, the bed 612 can automatically adjust, by the articulation controller, to one or more user-defined settings. As another example, the user can control the articulation controller to adjust the bed 612 to one or more user-defined positions. Sometimes, the bed 612 can be adjusted to one or more positions that may provide the user with improved or otherwise improve sleep and sleep quality. For example, a head portion on one side of the bed 612 can be automatically articulated, by the articulation controller, when one or more sensors of the air bed system 600 detect that a user sleeping on that side of the bed 612 is snoring. As a result, the user's snoring can be mitigated so that the snoring does not wake up another user sleeping in the bed 612.

In some implementations, the bed 612 can be adjusted using one or more devices in communication with the articulation controller or instead of the articulation controller. For example, the user can change positions of one or more portions of the bed 612 using the remote control 622 described above. The user can also adjust the bed 612 using a mobile application or other graphical user interface presented at a mobile computing device of the user.

The articulation controller can also provide different levels of massage to one or more portions of the bed 612 for one or more users. The user(s) can adjust one or more massage settings for the portions of the bed 612 using the remote control 622 and/or a mobile device in communication with the air bed system 600.

Examples of Data Processing Systems Associated with a Bed

Described are example systems and components for data processing tasks that are, for example, associated with a bed. In some cases, multiple examples of a particular component or group of components are presented. Some examples are redundant and/or mutually exclusive alternatives. Connections between components are shown as examples to illustrate possible network configurations for allowing communication between components. Different formats of connections can be used as technically needed/desired. The connections generally indicate a logical connection that can be created with any technologically feasible format. For example, a network on a motherboard can be created with a printed circuit board, wireless data connections, and/or other types of network connections. Some logical connections are not shown for clarity (e.g., connections with power supplies and/or computer readable memory).

Figure 8A:
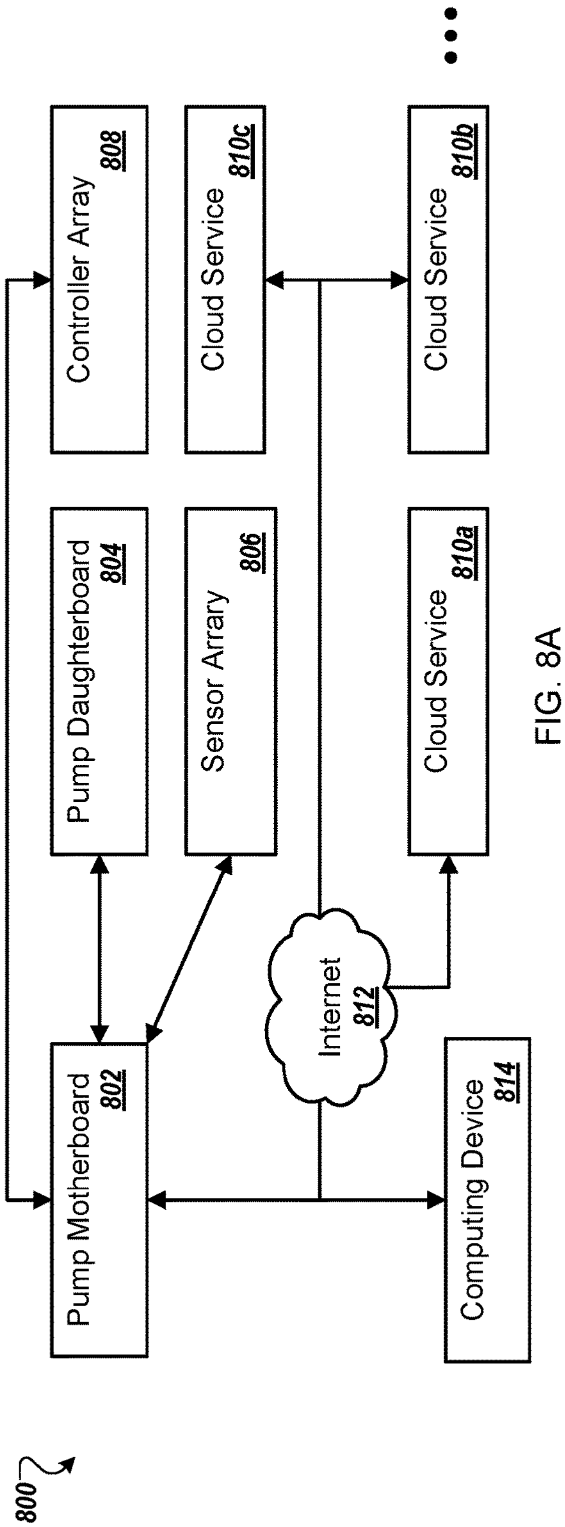
FIGS. 8A and 8B are block diagrams of example data processing systems that can be associated with a bed.
Figure 10:
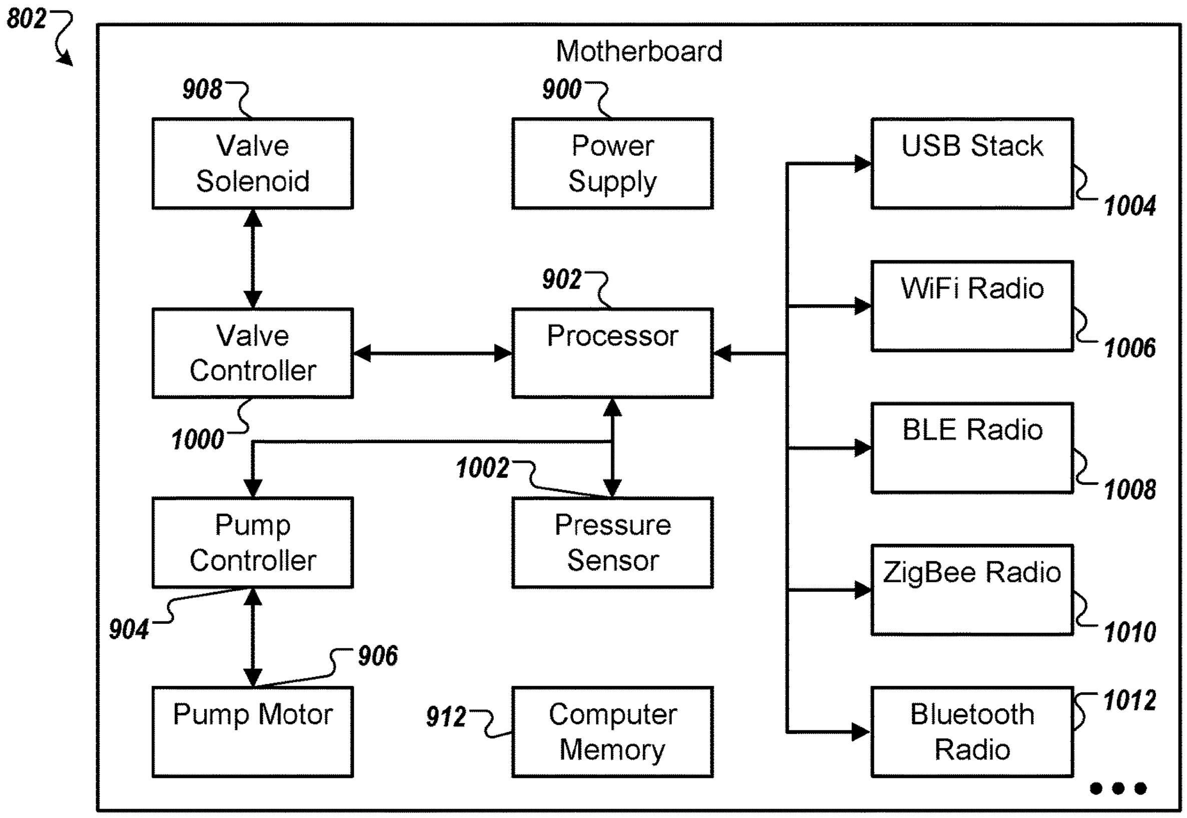
Figure 11:
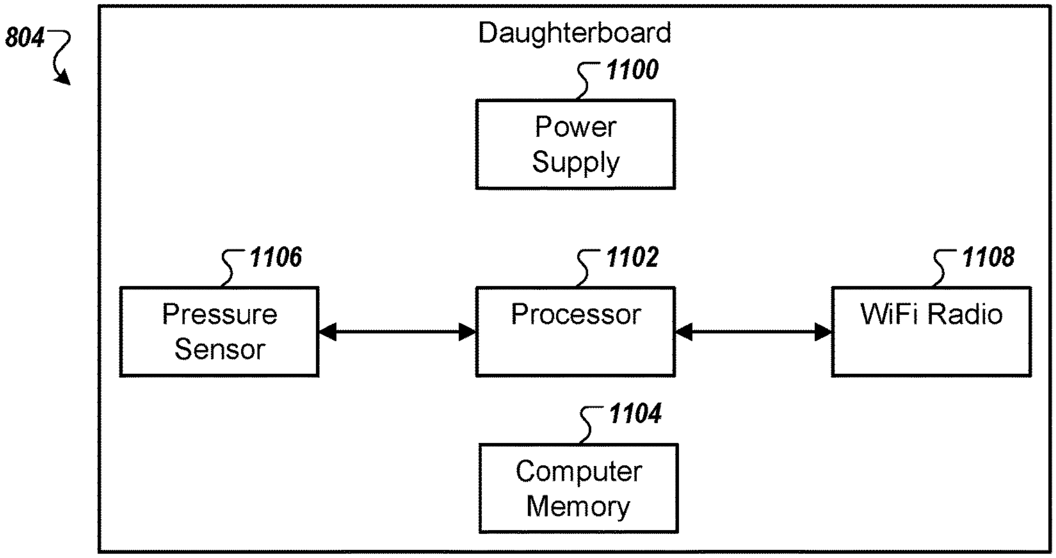
FIG. 11 is a block diagram of an example of a daughterboard that can be used in a data processing system associated with a bed.

FIG. 8A is a block diagram of an example data processing system 800 that can be associated with a bed system, including those described above (e.g., see FIGS. 10 and 11). The system 800 includes a pump motherboard 802 and a pump daughterboard 804. The system 800 includes a sensor array 806 having one or more sensors configured to sense physical phenomenon of the environment and/or bed, and to report sensing back to the pump motherboard 802 (e.g., for analysis). The sensor array 806 can include one or more different types of sensors, including but not limited to pressure, temperature, light, movement (e.g. motion), and audio. The system 800 also includes a controller array 808 that can include one or more controllers configured to control logic-controlled devices of the bed and/or environment (e.g., home automation devices, security systems light systems, and other devices). The pump motherboard 802 can be in communication with computing devices 814 and cloud services 810 over local networks (e.g., Internet 812) or otherwise as is technically appropriate.

In FIG. 8A, the pump motherboard 802 and daughterboard 804 are communicably coupled. They can be conceptually described as a center or hub of the system 800, with the other components conceptually described as spokes of the system 800. This can mean that each spoke component communicates primarily or exclusively with the pump motherboard 802. For example, a sensor of the sensor array 806 may not be configured to, or may not be able to, communicate directly with a corresponding controller. Instead, the sensor can report a sensor reading to the motherboard 802, and the motherboard 802 can determine that, in response, a controller of the controller array 808 should adjust some parameters of a logic controlled device or otherwise modify a state of one or more peripheral devices.

One advantage of a hub-and-spoke network configuration, or a star-shaped network, is a reduction in network traffic compared to, for example, a mesh network with dynamic routing. If a particular sensor generates a large, continuous stream of traffic, that traffic is transmitted over one spoke to the motherboard 802. The motherboard 802 can marshal and condense that data to a smaller data format for retransmission for storage in a cloud service 810. Additionally or alternatively, the motherboard 802 can generate a single, small, command message to be sent down a different spoke in response to the large stream. For example, if the large stream of data is a pressure reading transmitted from the sensor array 806 a few times a second, the motherboard 802 can respond with a single command message to the controller array 808 to increase the pressure in an air chamber of the bed. In this case, the single command message can be orders of magnitude smaller than the stream of pressure readings.

As another advantage, a hub-and-spoke network configuration can allow for an extensible network that accommodates components being added, removed, failing, etc. This can allow more, fewer, or different sensors in the sensor array 806, controllers in the controller array 808, computing devices 814, and/or cloud services 810. For example, if a particular sensor fails or is deprecated by a newer version, the system 800 can be configured such that only the motherboard 802 needs to be updated about the replacement sensor. This can allow product differentiation where the same motherboard 802 can support an entry level product with fewer sensors and controllers, a higher value product with more sensors and controllers, and customer personalization where a customer can add their own selected components to the system 800.

Additionally, a line of air bed products can use the system 800 with different components. In an application in which every air bed in the product line includes both a central logic unit and a pump, the motherboard 802 (and optionally the daughterboard 804) can be designed to fit within a single, universal housing. For each upgrade of the product in the product line, additional sensors, controllers, cloud services, etc., can be added. Design, manufacturing, and testing time can be reduced by designing all products in a product line from this base, compared to a product line in which each product has a bespoke logic control system.

Each of the components discussed above can be realized in a wide variety of technologies and configurations. Below, some examples of each component are discussed. Sometimes, two or more components of the system 800 can be realized in a single alternative component; some components can be realized in multiple, separate components; and/or some functionality can be provided by different components.

Figure 8B:
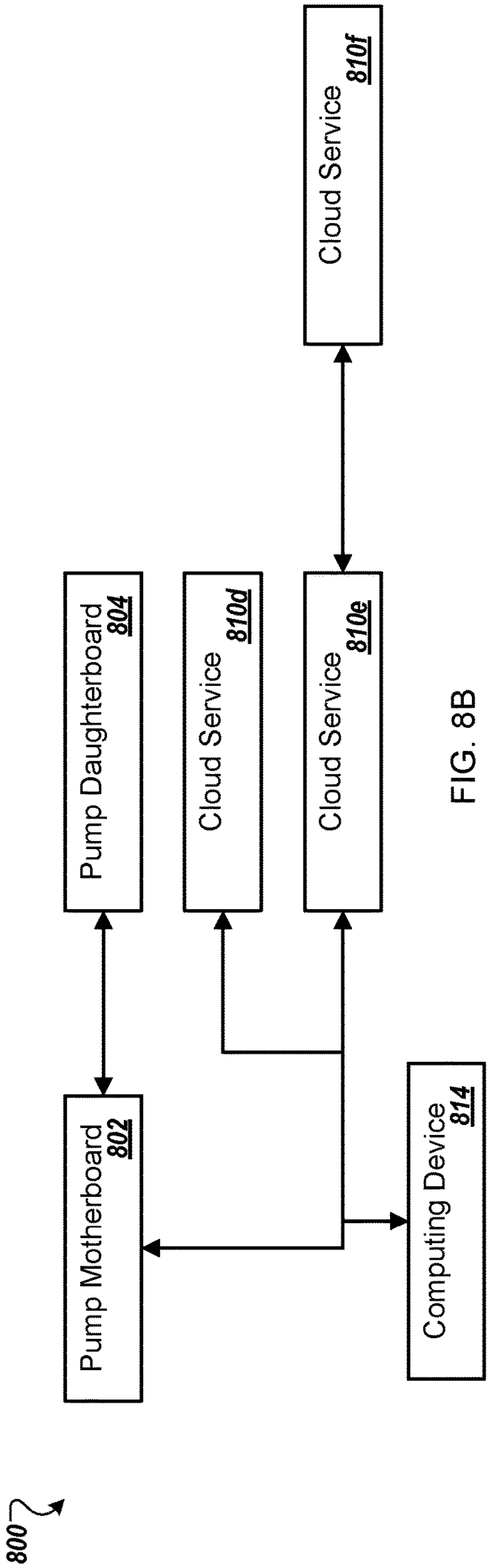

FIG. 8B is a block diagram showing communication paths of the system 800. As described, the motherboard 802 and daughterboard 804 may act as a hub of the system 800. When the pump daughterboard 804 communicates with cloud services 810 or other components, communications may be routed through the motherboard 802. This may allow the bed to have a single connection with the Internet 812. The computing device 814 may also have a connection to the Internet 812, possibly through the same gateway used by the bed and/or a different gateway (e.g., a cell service provider).

In FIG. 8B, cloud services 810*d* and 810*e* may be configured such that the motherboard 802 communicates with the cloud service directly (e.g., without having to use another cloud service 810 as an intermediary). Additionally or alternatively, some cloud services 810 (e.g., 810*f*) may only be reachable by the motherboard 802 through an intermediary cloud service (e.g., 810*e*). While not shown here, some cloud services 810 may be reachable either directly or indirectly by the pump motherboard 802.

Additionally, some or all of the cloud services 810 may communicate with other cloud services, including the transfer of data and/or remote function calls according to any technologically appropriate format. For example, one cloud service 810 may request a copy for another cloud service's 810 data (e.g., for purposes of backup, coordination, migration, calculations, data mining). Many cloud services 810 may also contain data that is indexed according to specific users tracked by the user account cloud 810*c* and/or the bed data cloud 810*a*. These cloud services 810 may communicate with the user account cloud 810*c* and/or the bed data cloud 810*a* when accessing data specific to a particular user or bed.

Figure 9:
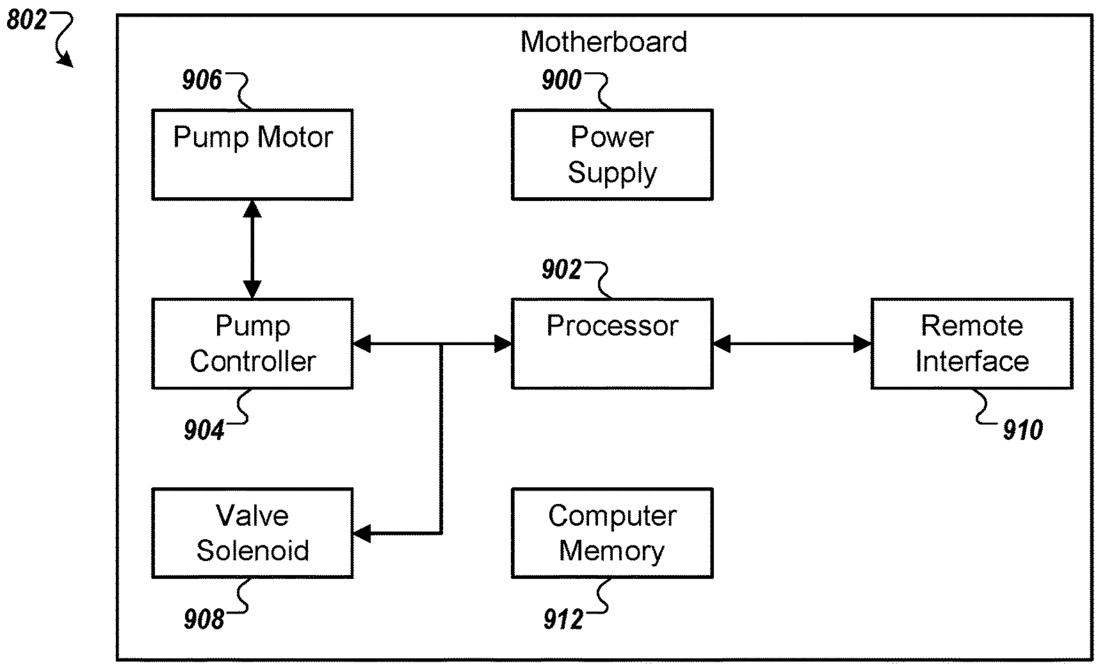
FIGS. 9 and 10 are block diagrams of examples of motherboards that can be used in a data processing system associated with a bed.

FIG. 9 is a block diagram of an example motherboard 802 in a data processing system associated with a bed system (e.g., refer to FIGS. 10 and 11). In this example, compared to other examples described below, this motherboard 802 consists of relatively fewer parts and can be limited to provide a relatively limited feature set.

The motherboard 802 includes a power supply 900, a processor 902, and computer memory 912. In general, the power supply 900 includes hardware used to receive electrical power from an outside source and supply it to components of the motherboard 802. The power supply may include a battery pack and/or wall outlet adapter, an AC to DC converter, a DC to AC converter, a power conditioner, a capacitor bank, and/or one or more interfaces for providing power in the current type, voltage, etc., needed by other components of the motherboard 802.

The processor 902 is generally a device for receiving input, performing logical determinations, and providing output. The processor 902 can be a central processing unit, a microprocessor, general purpose logic circuitry, application-specific integrated circuitry, a combination of these, and/or other hardware.

The memory 912 is generally one or more devices for storing data, which may include long term stable data storage (e.g., on a hard disk), short term unstable (e.g., on Random Access Memory), or any other technologically appropriate configuration.

The motherboard 802 includes a pump controller 904 and a pump motor 906. The pump controller 904 can receive commands from the processor 902 to control functioning of the pump motor 906. For example, the pump controller 904 can receive a command to increase pressure of an air chamber by 0.3 pounds per square inch (PSI). The pump controller 904, in response, engages a valve so that the pump motor 906 pumps air into the selected air chamber, and can engage the pump motor 906 for a length of time that corresponds to 0.3 PSI or until a sensor indicates that pressure has been increased by 0.3 PSI. Sometimes, the message can specify that the chamber should be inflated to a target PSI, and the pump controller 904 can engage the pump motor 906 until the target PSI is reached.

A valve solenoid 908 can control which air chamber a pump is connected to. In some cases, the solenoid 908 can be controlled by the processor 902 directly. In some cases, the solenoid 908 can be controlled by the pump controller 904.

A remote interface 910 of the motherboard 802 can allow the motherboard 802 to communicate with other components of a data processing system. For example, the motherboard 802 can be able to communicate with one or more daughterboards, with peripheral sensors, and/or with peripheral controllers through the remote interface 910. The remote interface 910 can provide any technologically appropriate communication interface, including but not limited to multiple communication interfaces such as WIFI, Bluetooth, and copper wired networks.

FIG. 10 is a block diagram of another example motherboard 802. Compared to the motherboard 802 in FIG. 9, the motherboard 802 in FIG. 10 can contain more components and provide more functionality in some applications.

This motherboard 802 can further include a valve controller 1000, a pressure sensor 1002, a universal serial bus (USB) stack 1004, a WiFi radio 1006, a Bluetooth Low Energy (BLE) radio 1008, a ZigBee radio 1010, a Bluetooth radio 1012, and a computer memory 912.

The valve controller 1000 can convert commands from the processor 902 into control signals for the valve solenoid 908. For example, the processor 902 can issue a command to the valve controller 1000 to connect the pump to a particular air chamber out of a group of air chambers in an air bed. The valve controller 1000 can control the position of the valve solenoid 908 so the pump is connected to the indicated air chamber.

The pressure sensor 1002 can read pressure readings from one or more air chambers of the air bed. The pressure sensor 1002 can also preform digital sensor conditioning. As described herein, multiple pressure sensors 1002 can be included as part of the motherboard 802 or otherwise in communication with the motherboard 802.

The motherboard 802 can include a suite of network interfaces 1004, 1006, 1008, 1010, 1012, etc., including but not limited to those shown in FIG. 10. These network interfaces can allow the motherboard to communicate over a wired or wireless network with any devices, including but not limited to peripheral sensors, peripheral controllers, computing devices, and devices and services connected to the Internet 812.

FIG. 11 is a block diagram of an example daughterboard 804 used in a data processing system associated with a bed system described herein. One or more daughterboards 804 can be connected to the motherboard 802. Some daughterboards 804 can be designed to offload particular and/or compartmentalized tasks from the motherboard 802. This can be advantageous if the particular tasks are computationally intensive, proprietary, or subject to future revisions. For example, the daughterboard 804 can be used to calculate a particular sleep data metric. This metric can be computationally intensive, and calculating the metric on the daughterboard 804 can free up resources of the motherboard 802 while the metric is calculated. The sleep metric may be subject to future revisions. To update the system 800 with the new metric, it is possible that only the daughterboard 804 calculates the metric to be replaced. In this case, the same motherboard 802 and other components can be used, saving the need to perform unit testing of additional components instead of just the daughterboard 804.

The daughterboard 804 includes a power supply 1100, a processor 1102, computer readable memory 1104, a pressure sensor 1106, and a WiFi radio 1108. The processor 1102 can use the pressure sensor 1106 to gather information about pressure of air bed chambers. The processor 1102 can perform an algorithm to calculate a sleep metric (e.g., sleep quality, bed presence, whether the user fell asleep, a heartrate, a respiration rate, movement, etc.). Sometimes, the sleep metric can be calculated from only air chamber pressure. The sleep metric can also be calculated using signals from a variety of sensors (e.g., movement, pressure, temperature, and/or audio sensors). The processor 1102 can receive that data from sensors that may be internal to the daughterboard 804, accessible via the WiFi radio 1108, or otherwise in communication with the processor 1102. Once the sleep metric is calculated, the processor 1102 can report that sleep metric to, for example, the motherboard 802. The motherboard 802 can generate instructions for outputting the sleep metric to the user or using the sleep metric to determine other user information or controls to control the bed and/or peripheral devices.

Figure 12:
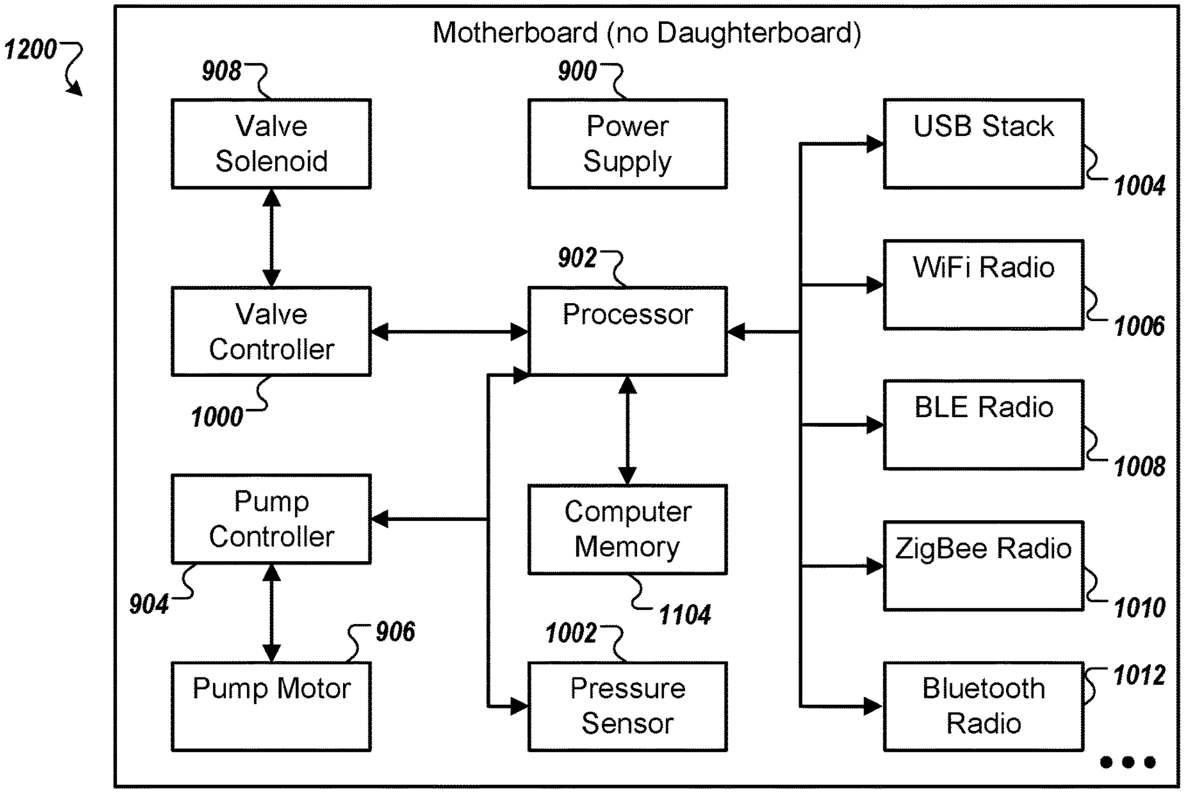
FIG. 12 is a block diagram of an example of a motherboard with no daughterboard that can be used in a data processing system associated with a bed.

FIG. 12 is a block diagram of an example motherboard 1200 with no daughterboard used in a data processing system associated with a bed system. In this example, the motherboard 1200 can perform most, all, or more of the features described with reference to the motherboard 802 in FIG. 10 and the daughterboard 804 in FIG. 11.

Figure 13:
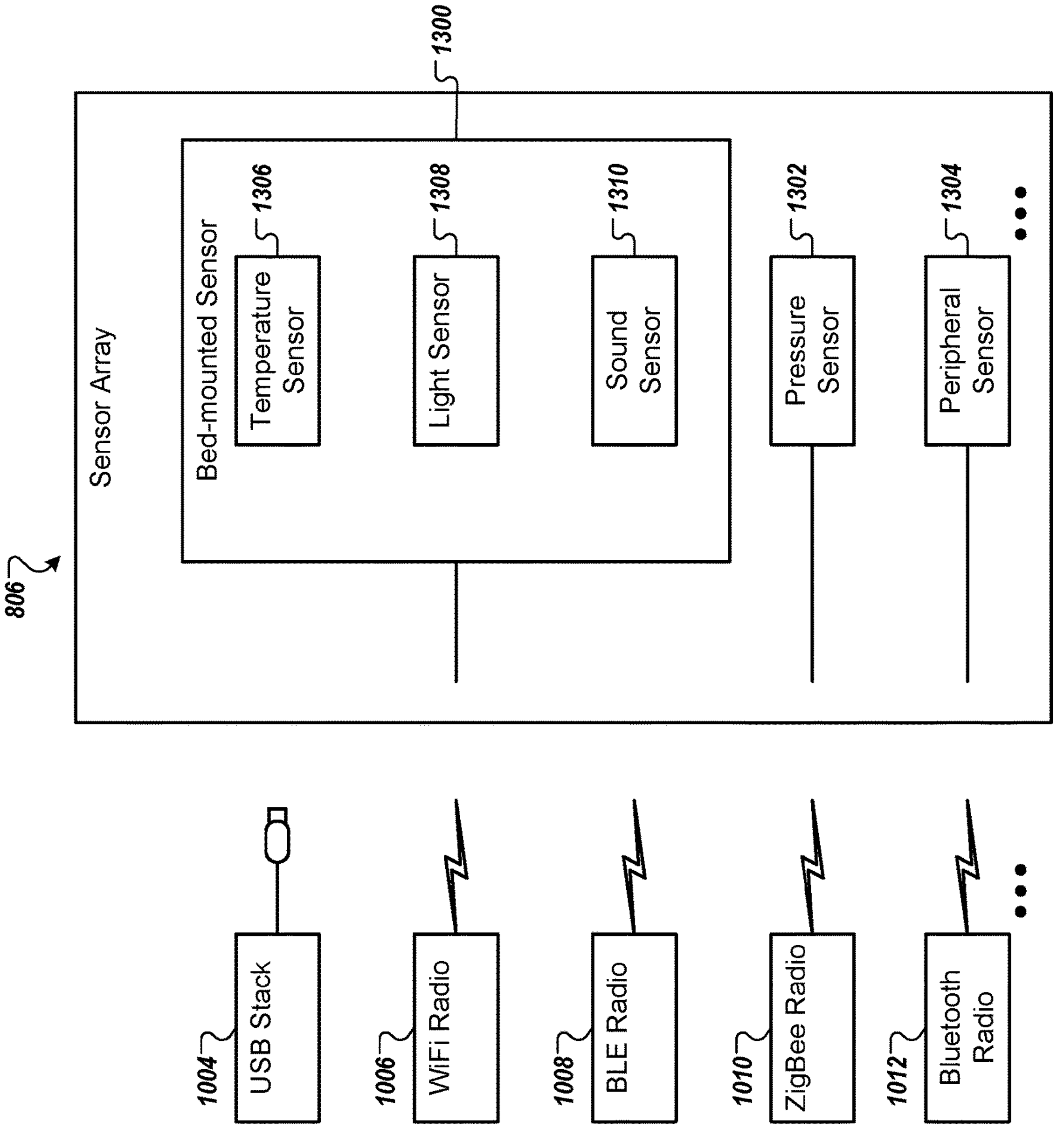
FIG. 13 is a block diagram of an example of a sensory array that can be used in a data processing system associated with a bed.

FIG. 13 is a block diagram of an example sensory array 806 used in a data processing system associated with a bed system described herein. The sensor array 806 is a conceptual grouping of some or all peripheral sensors that communicate with the motherboard 802 but are not native to the motherboard 802. The peripheral sensors 1302, 1304, 1306, 1308, 1310, etc. of the sensor array 806 communicate with the motherboard 802 through one or more network interfaces 1004, 1006, 1008, 1010, and 1012 of the motherboard, as is appropriate for the configuration of the particular sensor. For example, a sensor that outputs a reading over a USB cable can communicate through the USB stack 1004.

Some peripheral sensors of the sensor array 806 can be bed mounted sensors 1300 (e.g., temperature sensor 1306, light sensor 1308, sound sensor 1310). The bed mounted sensors 1300 can be embedded into a bed structure and sold with the bed, or later affixed to the structure (e.g., part of a pressure sensing pad that is removably installed on a top surface of the bed, part of a temperature sensing or heating pad that is removably installed on the top surface of the bed, integrated into the top surface, attached along connecting tubes between a pump and air chambers, within air chambers, attached to a headboard, attached to one or more regions of an adjustable foundation). One or more of the sensors 1302 can be load cells or force sensors as described in FIG. 13C. Other sensors 1302 and 1304 may not be mounted to the bed and can include a pressure sensor 1302 and/or peripheral sensor 1304. For example, the sensors 1302 and 1304 can be integrated or otherwise part of a user mobile device (e.g., mobile phone, wearable device). The sensors 1302 and 1304 can also be part of a central controller for controlling the bed and peripheral devices. Sometimes, the sensors 1302 and 1304 can be part of one or more home automation devices or other peripheral devices.

Sometimes, some or all of the bed mounted sensors 1300 and/or sensors 1302 and 1304 share networking hardware (e.g., a conduit that contains wires from each sensor, a multi-wire cable or plug that, when affixed to the motherboard 802, connect all the associated sensors with the motherboard 802). One, some, or all the sensors 1302, 1304, 1306, 1308, and 1310 can sense features of a mattress (e.g., pressure, temperature, light, sound, and/or other features) and features external to the mattress. Sometimes, pressure sensor 1302 can sense pressure of the mattress while some or all the sensors 1302, 1304, 1306, 1308, and 1310 sense features of the mattress and/or features external to the mattress.

Figure 14:
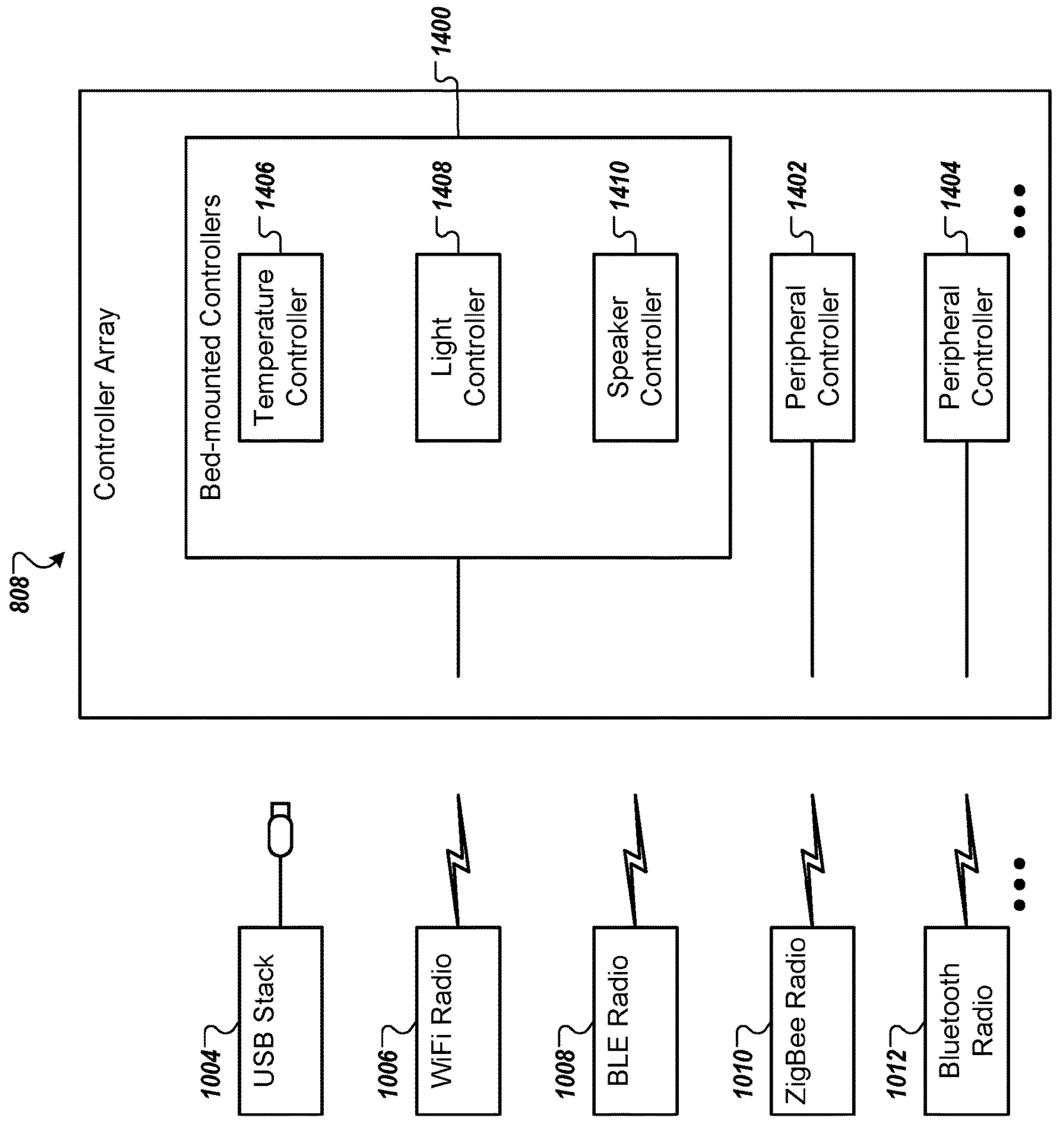
FIG. 14 is a block diagram of an example of a control array that can be used in a data processing system associated with a bed

FIG. 14 is a block diagram of an example controller array 808 used in a data processing system associated with a bed system. The controller array 808 is a conceptual grouping of some or all peripheral controllers that communicate with the motherboard 802 but are not native to the motherboard 802. The peripheral controllers can communicate with the motherboard 802 through one or more of the network interfaces 1004, 1006, 1008, 1010, and 1012 of the motherboard, as is appropriate for the configuration of the particular controller. Some of the controllers can be bed mounted controllers 1400, such as a temperature controller 1406, a light controller 1408, and a speaker controller 1410, as described in reference to bed-mounted sensors in FIG. 13A. Peripheral controllers 1402 and 1404 can be in communication with the motherboard 802, but optionally not mounted to the bed.

Figure 15:
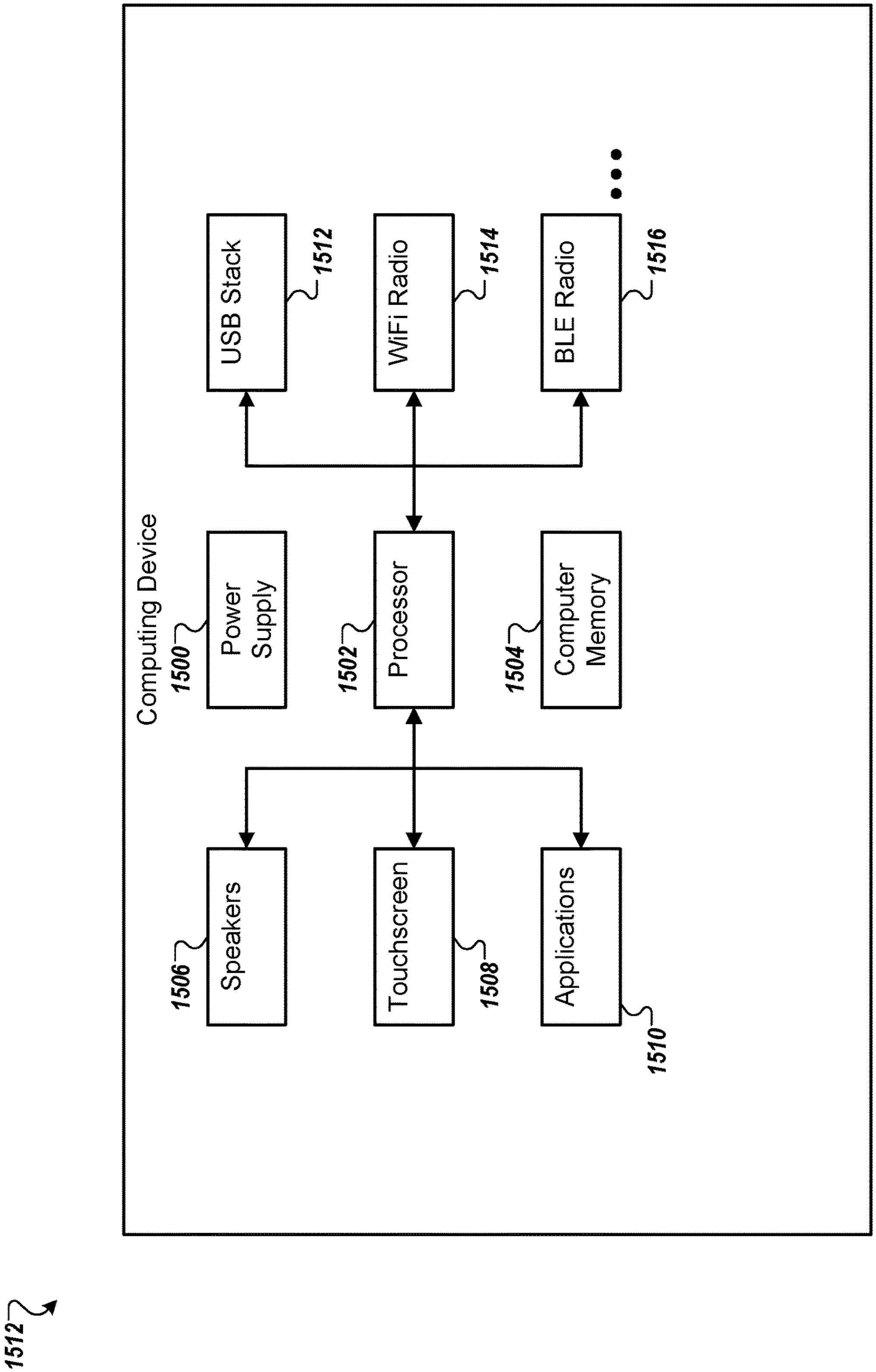
FIG. 15 is a block diagram of an example of a computing device that can be used in a data processing system associated with a bed.

FIG. 15 is a block diagram of an example computing device 1512 used in a data processing system associated with a bed system. The computing device 1512 can include computing devices used by a user of a bed including but not limited to mobile computing devices (e.g., mobile phones, tablet computers, laptops, smart phones, wearable devices), desktop computers, home automation devices, and/or central controllers or other hub devices.

The computing device 1512 includes a power supply 1500, a processor 1502, and computer readable memory 1504. User input and output can be transmitted by speakers 1506, a touchscreen 1508, or other not shown components (e.g., a pointing device or keyboard). The computing device 1512 can run applications 1510 including, for example, applications to allow the user to interact with the system 800. These applications can allow a user to view information about the bed (e.g., sensor readings, sleep metrics), information about themselves (e.g., health conditions detected based on signals sensed at the bed), and/or configure the system 800 behavior (e.g., set desired firmness, set desired behavior for peripheral devices). The computing device 1512 can be used in addition to, or to replace, the remote control 162 described above.

Figure 16:
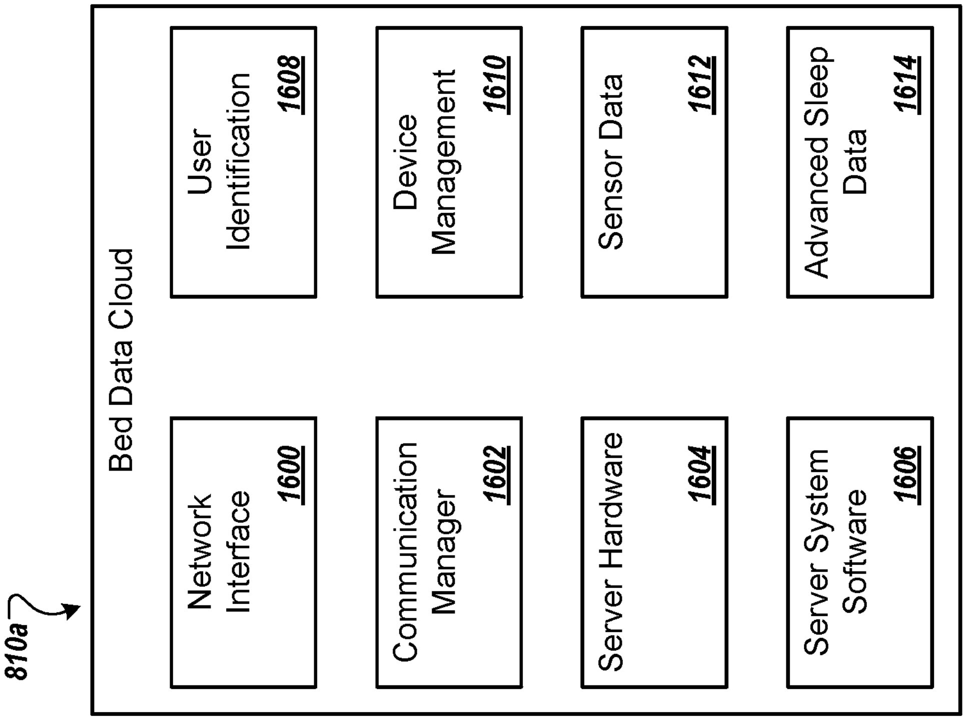

FIG. 16 is a block diagram of an example bed data cloud service 810*a* used in a data processing system associated with a bed system. Here, the bed data cloud service 810*a* is configured to collect sensor data and sleep data from a particular bed, and to match the data with one or more users that used the bed when the data was generated.

The bed data cloud service 810*a* includes a network interface 1600, a communication manager 1602, server hardware 1604, and server system software 1606. The bed data cloud service 810*a* is also shown with a user identification module 1608, a device management 1610 module, a sensor data module 1610, and an advanced sleep data module 1614. The network interface 1600 includes hardware and low level software to allow hardware devices (e.g., components of the service 810*a*) to communicate over networks (e.g., with each other, with other destinations over the Internet 812). The network interface 1600 can include network cards, routers, modems, and other hardware. The communication manager 1602 generally includes hardware and software that operate above the network interface 1600 such as software to initiate, maintain, and tear down network communications used by the service 810*a* (e.g., TCP/IP, SSL or TLS, Torrent, and other communication sessions over local or wide area networks). The communication manager 1602 can also provide load balancing and other services to other elements of the service 810*a*. The server hardware 1604 generally includes physical processing devices used to instantiate and maintain the service 810*a*. This hardware includes, but is not limited to, processors (e.g., central processing units, ASICs, graphical processers) and computer readable memory (e.g., random access memory, stable hard disks, tape backup). One or more servers can be configured into clusters, multi-computer, or datacenters that can be geographically separate or connected. The server system software 1606 generally includes software that runs on the server hardware 1604 to provide operating environments to applications and services (e.g., operating systems running on real servers, virtual machines instantiated on real servers to create many virtual servers, server level operations such as data migration, redundancy, and backup).

The user identification 1608 can include, or reference, data related to users of beds with associated data processing systems. The users may include customers, owners, or other users registered with the service 810*a* or another service. Each user can have a unique identifier, user credentials, contact information, billing information, demographic information, or any other technologically appropriate information.

The device manager 1610 can include, or reference, data related to beds or other products associated with data processing systems. The beds can include products sold or registered with a system associated with the service 810*a*. Each bed can have a unique identifier, model and/or serial number, sales information, geographic information, delivery information, a listing of associated sensors and control peripherals, etc. An index or indexes stored by the service 810*a* can identify users associated with beds. This index can record sales of a bed to a user, users that sleep in a bed, etc.

The sensor data 1612 can record raw or condensed sensor data recorded by beds with associated data processing systems. For example, a bed's data processing system can have temperature, pressure, motion, audio, and/or light sensors. Readings from these sensors, either in raw form or in a format generated from the raw data (e.g. sleep metrics), can be communicated by the bed's data processing system to the service 810*a* for storage in the sensor data 1612. An index or indexes stored by the service 810*a* can identify users and/or beds associated with the sensor data 1612.

The service 810*a* can use any of its available data (e.g., sensor data 1612) to generate advanced sleep data 1614. The advanced sleep data 1614 includes sleep metrics and other data generated from sensor readings (e.g., health information). Some of these calculations can be performed in the service 810*a* instead of locally on the bed's data processing system because the calculations can be computationally complex or require a large amount of memory space or processor power that may not be available on the bed's data processing system. This can help allow a bed system to operate with a relatively simple controller while being part of a system that performs relatively complex tasks and computations.

For example, the service 810*a* can retrieve one or more machine learning models from a remote data store and use those models to determine the advanced sleep data 1614. The service 810*a* can retrieve one or more models to determine overall sleep quality of the user based on currently detected sensor data 1612 and/or historic sensor data. The service 810*a* can retrieve other models to determine whether the user is snoring based on the detected sensor data 1612. The service 810*a* can retrieve other models to determine whether the user experiences a health condition based on the data 1612.

Figure 17:
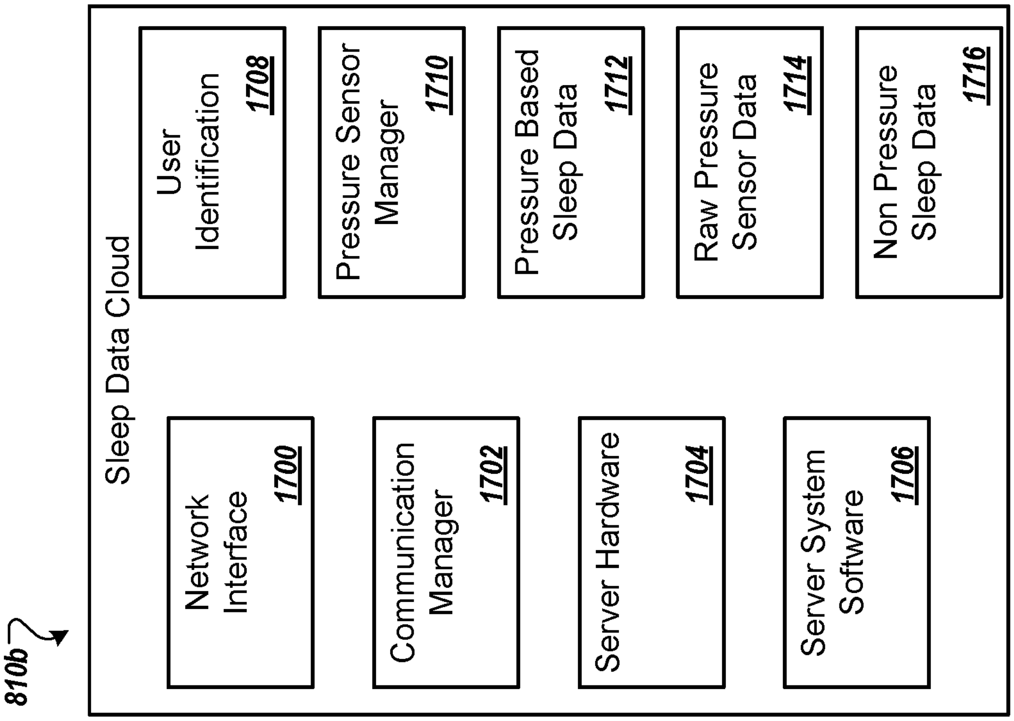
FIGS. 16-20 are block diagrams of example cloud services that can be used in a data processing system associated with a bed.

FIG. 17 is a block diagram of an example sleep data cloud service 810*b* used in a data processing system associated with a bed system. Here, the sleep data cloud service 810*b* is configured to record data related to users' sleep experience. The service 810*b* includes a network interface 1700, a communication manager 1702, server hardware 1704, and server system software 1706. The service 810*b* also includes a user identification module 1708, a pressure sensor manager 1710, a pressure based sleep data module 1712, a raw pressure sensor data module 1714, and a non-pressure sleep data module 1716. Sometimes, the service 810*b* can include a sensor manager for each sensor. The service 810*b* can also include a sensor manager that relates to multiple sensors in beds (e.g., a single sensor manager can relate to pressure, temperature, light, movement, and audio sensors in a bed).

The pressure sensor manager 1710 can include, or reference, data related to the configuration and operation of pressure sensors in beds. This data can include an identifier of the types of sensors in a particular bed, their settings and calibration data, etc. The pressure based sleep data 1712 can use raw pressure sensor data 1714 to calculate sleep metrics tied to pressure sensor data. For example, user presence, movements, weight change, heartrate, and breathing rate can be determined from raw pressure sensor data 1714. An index or indexes stored by the service 810*b* can identify users associated with pressure sensors, raw pressure sensor data, and/or pressure based sleep data. The non-pressure sleep data 1716 can use other sources of data to calculate sleep metrics. User-entered preferences, light sensor readings, and sound sensor readings can be used to track sleep data. User presence can also be determined from a combination of raw pressure sensor data 1714 and non-pressure sleep data 1716 (e.g., raw temperature data). Sometimes, bed presence can be determined using only the temperature data. Changes in temperature data can be monitored to determine bed presence or absence in a temporal interval (e.g., window of time) of a given duration. The temperature and/or pressure data can also be combined with other sensing modalities or motion sensors that reflect different forms of movement (e.g., load cells) to accurately detect user presence. For example, the temperature and/or pressure data can be provided as input to a bed presence classifier, which can determine user bed presence based on real-time or near real-time data collected at the bed. The classifier can be trained to differentiate the temperature data from the pressure data, identify peak values in the temperature and pressure data, and generate a bed presence indication based on correlating the peak values. The peak values can be within a threshold distance from each other to then generate an indication that the user is in the bed. An index or indexes stored by the service 810*b* can identify users associated with sensors and/or the data 1716.

Figure 18:
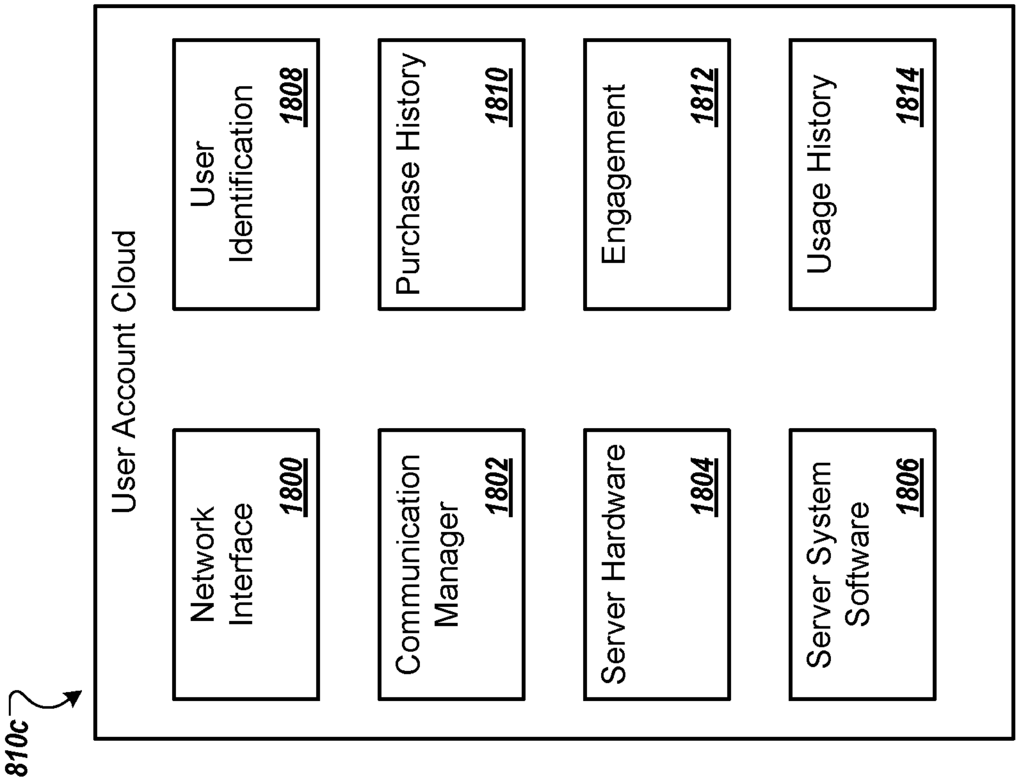

FIG. 18 is a block diagram of an example user account cloud service 810*c* used in a data processing system associated with a bed system. Here, the service 810*c* is configured to record a list of users and to identify other data related to those users. The service 810*c* includes a network interface 1800, a communication manager 1802, server hardware 1804, and server system software 1806. The service 810*c* also includes a user identification module 1808, a purchase history module 1810, an engagement module 1812, and an application usage history module 1814.

The user identification module 1808 can include, or reference, data related to users of beds with associated data processing systems, as described above. The purchase history module 1810 can include, or reference, data related to purchases by users. The purchase data can include a sale's contact information, billing information, and salesperson information associated with the user's purchase of the bed system. An index or indexes stored by the service 810*c* can identify users associated with a bed purchase.

The engagement module 1812 can track user interactions with the manufacturer, vendor, and/or manager of the bed/cloud services. This data can include communications (e.g., emails, service calls), data from sales (e.g., sales receipts, configuration logs), and social network interactions. The data can also include servicing, maintenance, or replacements of components of the user's bed system. The usage history module 1814 can contain data about user interactions with applications and/or remote controls of the bed. A monitoring and configuration application can be distributed to run on, for example, computing devices 814 described herein. The application can log and report user interactions for storage in the application usage history module 1814. An index or indexes stored by the service 810*c* can also identify users associated with each log entry. User interactions stored in the module 1814 can optionally be used to determine or predict user preferences and/or settings for the user's bed and/or peripheral devices that can improve the user's overall sleep quality.

Figure 19:
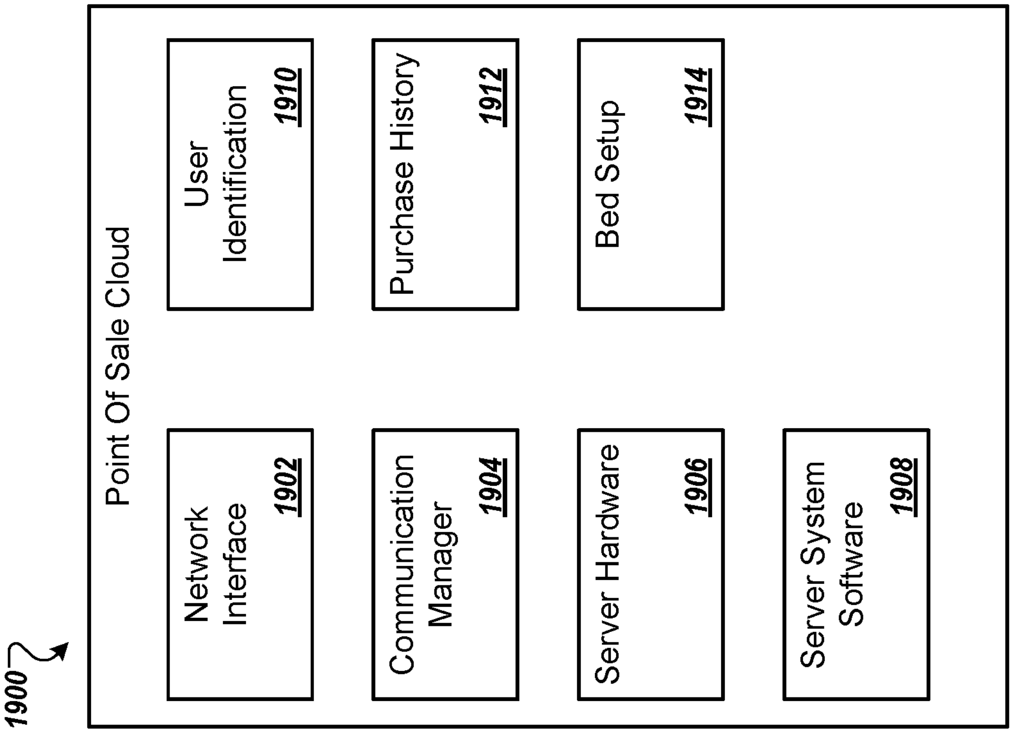

FIG. 19 is a block diagram of an example point of sale cloud service 1900 used in a data processing system associated with a bed system. Here, the service 1900 can record data related to users' purchases, specifically purchases of bed systems described herein. The service 1900 is shown with a network interface 1902, a communication manager 1904, server hardware 1906, and server system software 1908. The service 1900 also includes a user identification module 1910, a purchase history module 1912, and a bed setup module 1914.

The purchase history module 1912 can include, or reference, data related to purchases made by users identified in the module 1910, such as data of a sale, price, and location of sale, delivery address, and configuration options selected by the users at the time of sale. The configuration options can include selections made by the user about how they wish their newly purchased beds to be setup and can include expected sleep schedule, a listing of peripheral sensors and controllers that they have or will install, etc.

The bed setup module 1914 can include, or reference, data related to installations of beds that users purchase. The bed setup data can include a date and address to which a bed is delivered, a person who accepts delivery, configuration that is applied to the bed upon delivery (e.g., firmness settings), name(s) of bed user(s), which side of the bed each user will use, etc. Data recorded in the service 1900 can be referenced by a user's bed system at later times to control functionality of the bed system and/or to send control signals to peripheral components. This can allow a salesperson to collect information from the user at the point of sale that later facilitates bed system automation. Sometimes, some or all aspects of the bed system can be automated with little or no user-entered data required after the point of sale. Sometimes, data recorded in the service 1900 can be used in connection with other, user-entered data.

Figure 20:
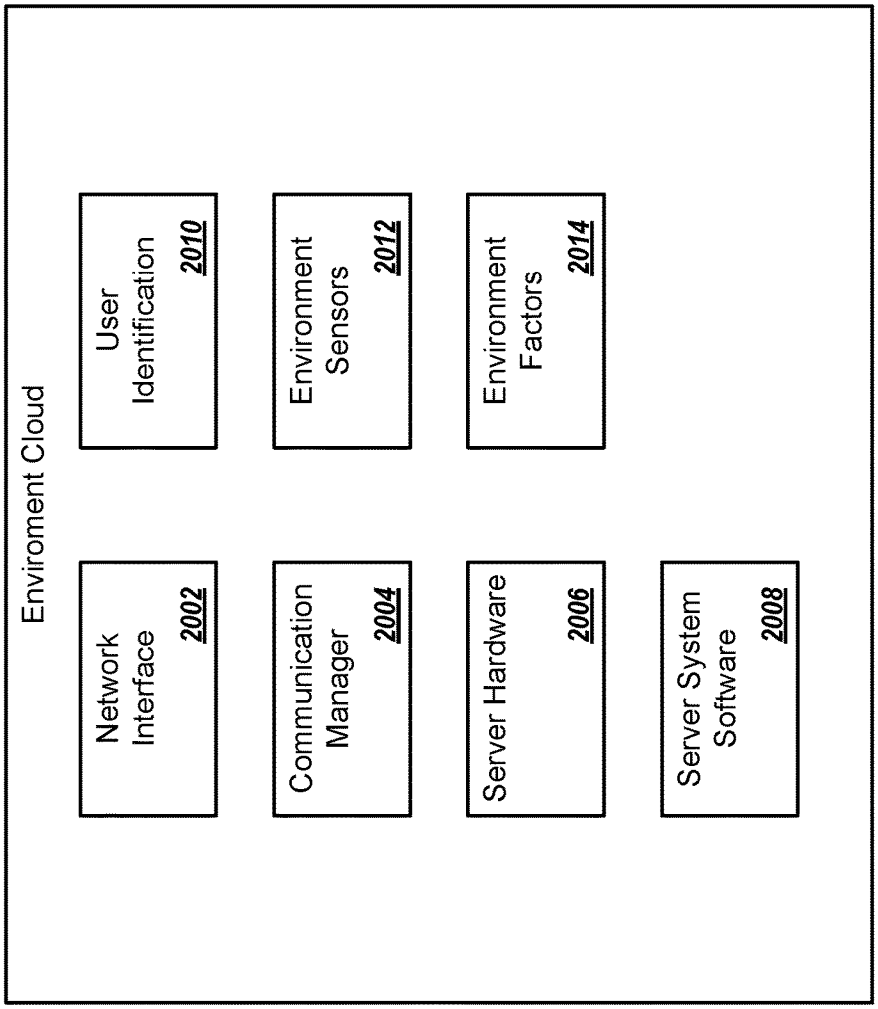

FIG. 20 is a block diagram of an example environment cloud service 2000 used in a data processing system associated with a bed system. Here, the service 2000 is configured to record data related to users' home environment. The service 2000 includes a network interface 2002, a communication manager 2004, server hardware 2006, and server system software 2008. The service 2000 also includes a user identification module 2010, an environmental sensors module 2012, and an environmental factors module 2014. The environmental sensors module 2012 can include a listing and identification of sensors that users identified in the module 2010 to have installed in and/or surrounding their bed (e.g., light, noise/audio, vibration, thermostats, movement/motion sensors). The module 2012 can also store historical readings or reports from the environmental sensors. The module 2012 can be accessed at a later time and used by one or more cloud services described herein to determine sleep quality and/or health information of the users. The environmental factors module 2014 can include reports generated based on data in the module 2012. For example, the module 2014 can generate and retain a report indicating frequency and duration of instances of increased lighting when the user is asleep based on light sensor data that is stored in the environment sensors module 2012.

In the examples discussed here, each cloud service 810 is shown with some of the same components. These same components can be partially or wholly shared between services, or they can be separate. Sometimes, each service can have separate copies of some or all the components that are the same or different in some ways. These components are provided as illustrative examples. In other examples, each cloud service can have different number, types, and styles of components that are technically possible.

Figure 21:
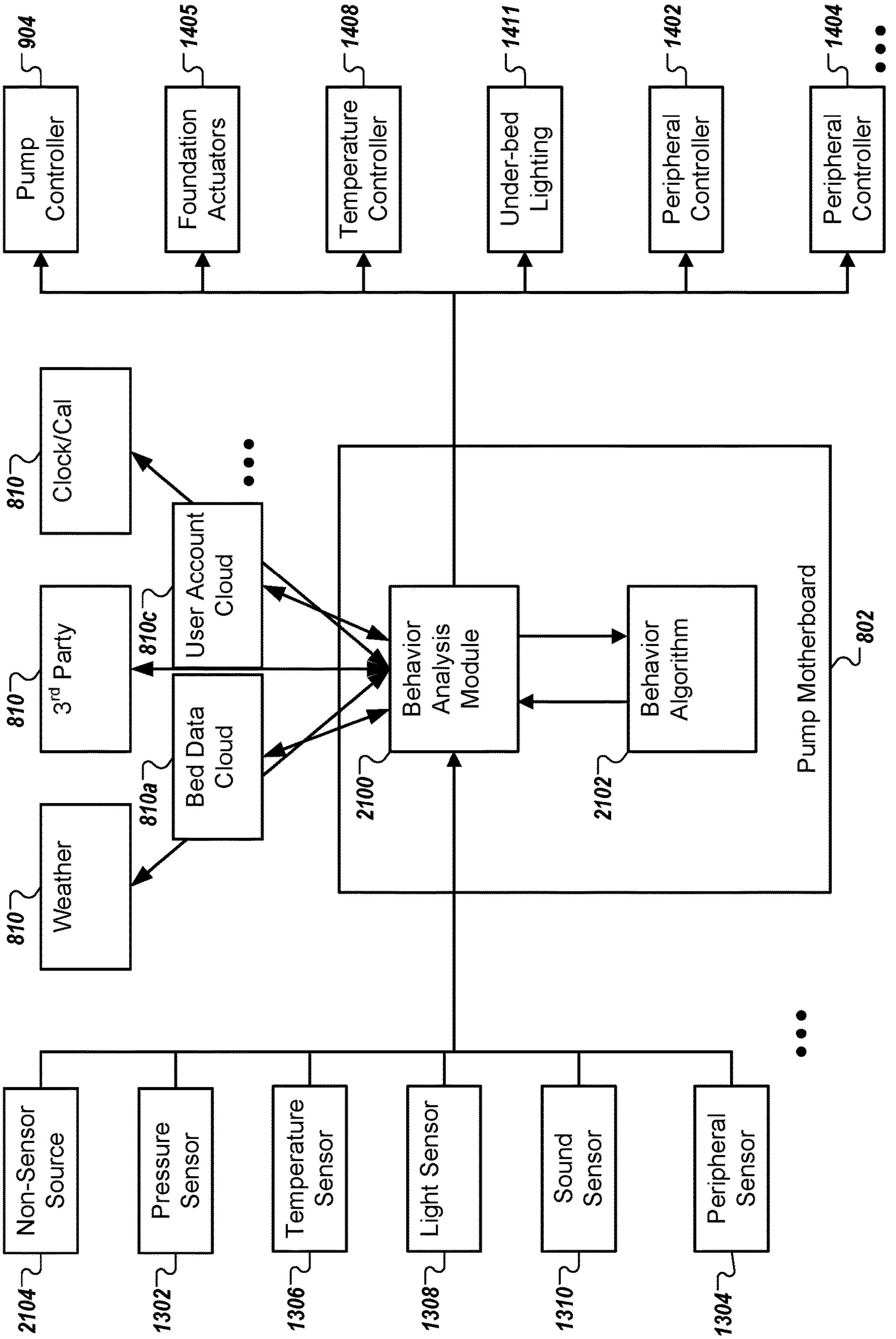
FIG. 21 is a block diagram of an example of using a data processing system that can be associated with a bed to automate peripherals around the bed.

FIG. 21 is a block diagram of an example of using a data processing system associated with a bed to automate peripherals around the bed. Shown here is a behavior analysis module 2100 that runs on the motherboard 802. The behavior analysis module 2100 can be one or more software components stored on the computer memory 912 and executed by the processor 902. In general, the module 2100 can collect data from a variety of sources (e.g., sensors 1302, 1304, 1306, 1308, and/or 1310, non-sensor local sources 2104, cloud data services 810*a* and/or 810*c*) and use a behavioral algorithm 2102 (e.g., machine learning model(s)) to generate actions to be taken (e.g., commands to send to peripheral controllers, data to send to cloud services, such as the bed data cloud 810*a* and/or the user account cloud 810*c*). This can be useful, for example, in tracking user behavior and automating devices in communication with the user's bed.

The module 2100 can collect data from any technologically appropriate source (e.g., sensors of the sensor array 806) to gather data about features of a bed, the bed's environment, and/or the bed's users. The data can provide the module 2100 with information about a current state of the bed's environment. For example, the module 2100 can access readings from the pressure sensor 1302 to determine air chamber pressure in the bed. From this reading, and potentially other data, user presence can be determined. In another example, the module 2100 can access the light sensor 1308 to detect the amount of light in the environment. The module 2100 can also access the temperature sensor 1306 to detect a temperature in the environment and/or microclimates in the bed. Using this data, the module 2100 can determine whether temperature adjustments should be made to the environment and/or components of the bed to improve the user's sleep quality and overall comfortability. Similarly, the module 2100 can access data from cloud services to make more accurate determinations of user sleep quality, health information, and/or control the bed and/or peripheral devices. For example, the behavior analysis module 2100 can access the bed cloud service 810*a* to access historical sensor data 1612 and/or advanced sleep data 1614. The module 2100 can also access a weather reporting service, a 3*r* d party data provider (e.g., traffic and news data, emergency broadcast data, user travel data), and/or a clock and calendar service. Using data retrieved from the cloud services 810, the module 2100 can accurately determine user sleep quality, health information, and/or control of the bed and/or peripheral devices. Similarly, the module 2100 can access data from non-sensor sources 2104, such as a local clock and calendar service (e.g., a component of the motherboard 802 or of the processor 902). The module 2100 can use this information to determine, for example, times of day that the user is in bed, asleep, waking up, and/or going to bed.

The behavior analysis module 2100 can aggregate and prepare this data for use with one or more behavioral algorithms 2102 (e.g., machine learning models). The behavioral algorithms 2102 can be used to learn a user's behavior and/or to perform some action based on the state of the accessed data and/or the predicted user behavior. For example, the behavior algorithm 2102 can use available data (e.g., pressure sensor, non-sensor data, clock and calendar data) to create a model of when a user goes to bed every night. Later, the same or a different behavioral algorithm 2102 can be used to determine if an increase in air chamber pressure is likely to indicate a user going to bed and, if so, send some data to a third-party cloud service 810 and/or engage a peripheral controller 1402 or 1404, foundation actuators 1405, a temperature controller 1408, and/or an under-bed lighting controller 1411.

Here, the module 2100 and the behavioral algorithm 2102 are shown as components of the motherboard 802. Other configurations are also possible. For example, the same or a similar behavioral analysis module 2100 and/or behavioral algorithm 2102 can be run in one or more cloud services, and resulting output can be sent to the pump motherboard 802, a controller in the controller array 808, or to any other technologically appropriate recipient described throughout this document.

Figure 22:
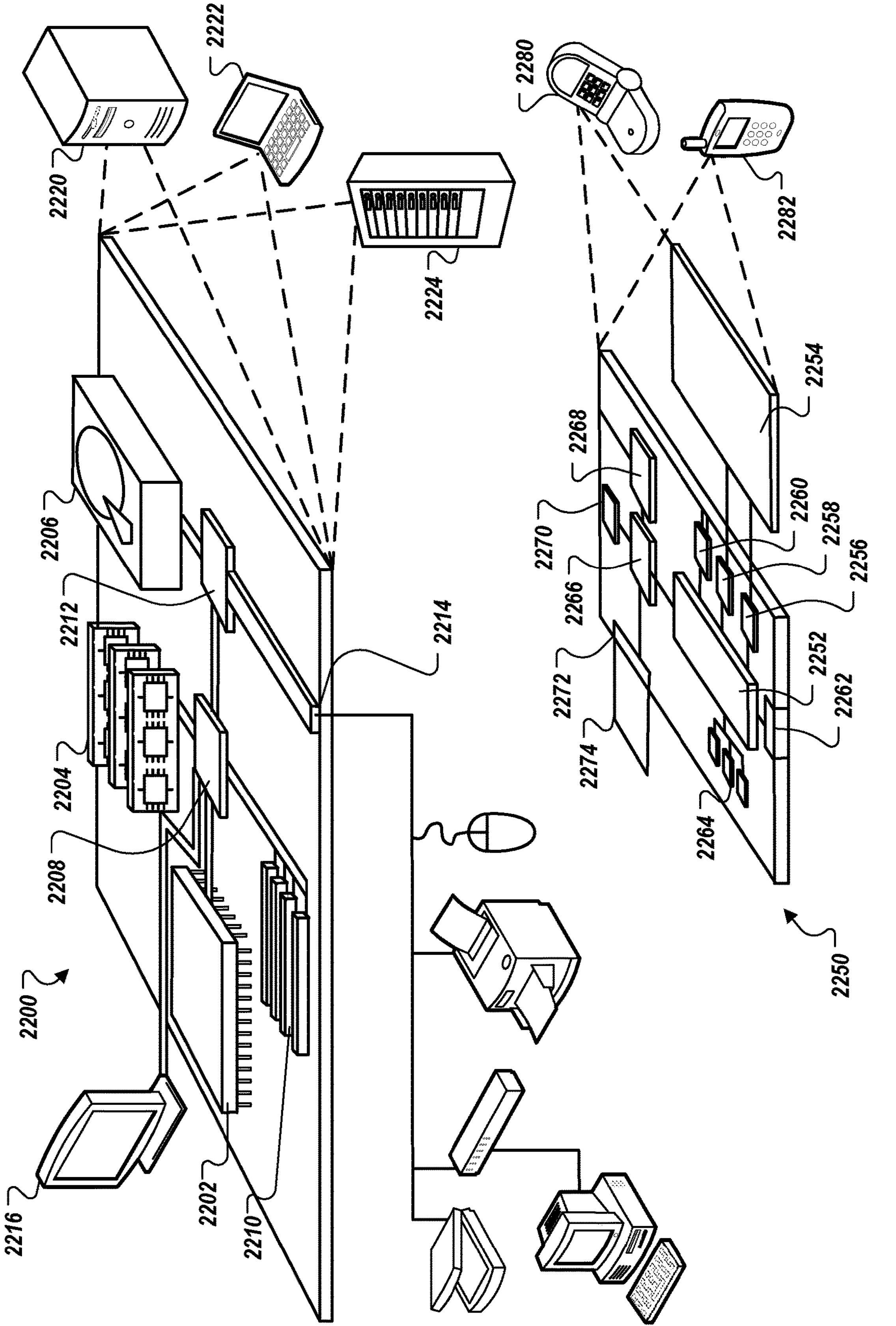
FIG. 22 is a schematic diagram that shows an example of a computing device and a mobile computing device.

FIG. 22 shows an example of a computing device 2200 and an example of a mobile computing device that can be used to implement the techniques described here. The computing device 2200 is intended to represent various forms of digital computers, such as laptops, desktops, workstations, personal digital assistants, servers, blade servers, mainframes, and other appropriate computers. The mobile computing device is intended to represent various forms of mobile devices, such as personal digital assistants, cellular telephones, smart-phones, and other similar computing devices. The components shown here, their connections and relationships, and their functions, are meant to be exemplary only, and are not meant to limit implementations of the inventions described and/or claimed in this document.

The computing device 2200 includes a processor 2202, a memory 2204, a storage device 2206, a high-speed interface 2208 connecting to the memory 2204 and multiple high-speed expansion ports 2210, and a low-speed interface 2212 connecting to a low-speed expansion port 2214 and the storage device 2206. Each of the processor 2202, the memory 2204, the storage device 2206, the high-speed interface 2208, the high-speed expansion ports 2210, and the low-speed interface 2212, are interconnected using various busses, and can be mounted on a common motherboard or in other manners as appropriate. The processor 2202 can process instructions for execution within the computing device 2200, including instructions stored in the memory 2204 or on the storage device 2206 to display graphical information for a GUI on an external input/output device, such as a display 2216 coupled to the high-speed interface 2208. In other implementations, multiple processors and/or multiple buses can be used, as appropriate, along with multiple memories and types of memory. Also, multiple computing devices can be connected, with each device providing portions of the necessary operations (e.g., as a server bank, a group of blade servers, or a multi-processor system). The memory 2204 stores information within the computing device 2200. In some implementations, the memory 2204 is a volatile memory unit or units. In some implementations, the memory 2204 is a non-volatile memory unit or units. The memory 2204 can also be another form of computer-readable medium, such as a magnetic or optical disk. The storage device 2206 is capable of providing mass storage for the computing device 2200. In some implementations, the storage device 2206 can be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product can also contain instructions that, when executed, perform one or more methods, such as those described above. The computer program product can also be tangibly embodied in a computer- or machine-readable medium, such as the memory 2204, the storage device 2206, or memory on the processor 2202.

The high-speed interface 2208 manages bandwidth-intensive operations for the computing device 2200, while the low-speed interface 2212 manages lower bandwidth-intensive operations. Such allocation of functions is exemplary only. In some implementations, the high-speed interface 2208 is coupled to the memory 2204, the display 2216 (e.g., through a graphics processor or accelerator), and to the high-speed expansion ports 2210, which can accept various expansion cards (not shown). In the implementation, the low-speed interface 2212 is coupled to the storage device 2206 and the low-speed expansion port 2214. The low-speed expansion port 2214, which can include various communication ports (e.g., USB, Bluetooth, Ethernet, wireless Ethernet) can be coupled to one or more input/output devices, such as a keyboard, a pointing device, a scanner, or a networking device such as a switch or router, e.g., through a network adapter. The computing device 2200 can be implemented in a number of different forms, as shown in the figure. For example, it can be implemented as a standard server 2220, or multiple times in a group of such servers. In addition, it can be implemented in a personal computer such as a laptop computer 2222. It can also be implemented as part of a rack server system 2224. Alternatively, components from the computing device 2200 can be combined with other components in a mobile device (not shown), such as a mobile computing device 2250. Each of such devices can contain one or more of the computing device 2200 and the mobile computing device 2250, and an entire system can be made up of multiple computing devices communicating with each other. The mobile computing device 2250 includes a processor 2252, a memory 2264, an input/output device such as a display 2254, a communication interface 2266, and a transceiver 2268, among other components. The mobile computing device 2250 can also be provided with a storage device, such as a micro-drive or other device, to provide additional storage. Each of the processor 2252, the memory 2264, the display 2254, the communication interface 2266, and the transceiver 2268, are interconnected using various buses, and several of the components can be mounted on a common motherboard or in other manners as appropriate.

The processor 2252 can execute instructions within the mobile computing device 2250, including instructions stored in the memory 2264. The processor 2252 can be implemented as a chip set of chips that include separate and multiple analog and digital processors. The processor 2252 can provide, for example, for coordination of the other components of the mobile computing device 2250, such as control of user interfaces, applications run by the mobile computing device 2250, and wireless communication by the mobile computing device 2250. The processor 2252 can communicate with a user through a control interface 2258 and a display interface 2256 coupled to the display 2254. The display 2254 can be, for example, a TFT (Thin-Film-Transistor Liquid Crystal Display) display or an OLED (Organic Light Emitting Diode) display, or other appropriate display technology. The display interface 2256 can comprise appropriate circuitry for driving the display 2254 to present graphical and other information to a user. The control interface 2258 can receive commands from a user and convert them for submission to the processor 2252. In addition, an external interface 2262 can provide communication with the processor 2252, so as to enable near area communication of the mobile computing device 2250 with other devices. The external interface 2262 can provide, for example, for wired communication in some implementations, or for wireless communication in other implementations, and multiple interfaces can also be used.

The memory 2264 stores information within the mobile computing device 2250. The memory 2264 can be implemented as one or more of a computer-readable medium or media, a volatile memory unit or units, or a non-volatile memory unit or units. An expansion memory 2274 can also be provided and connected to the mobile computing device 2250 through an expansion interface 2272, which can include, for example, a SIMM (Single In Line Memory Module) card interface. The expansion memory 2274 can provide extra storage space for the mobile computing device 2250, or can also store applications or other information for the mobile computing device 2250. Specifically, the expansion memory 2274 can include instructions to carry out or supplement the processes described above, and can include secure information also. Thus, for example, the expansion memory 2274 can be provide as a security module for the mobile computing device 2250, and can be programmed with instructions that permit secure use of the mobile computing device 2250. In addition, secure applications can be provided via the SIMM cards, along with additional information, such as placing identifying information on the SIMM card in a non-hackable manner.

The memory can include, for example, flash memory and/or NVRAM memory (non-volatile random access memory), as discussed below. In some implementations, a computer program product is tangibly embodied in an information carrier. The computer program product contains instructions that, when executed, perform one or more methods, such as those described above. The computer program product can be a computer- or machine-readable medium, such as the memory 2264, the expansion memory 2274, or memory on the processor 2252. In some implementations, the computer program product can be received in a propagated signal, for example, over the transceiver 2268 or the external interface 2262.

The mobile computing device 2250 can communicate wirelessly through the communication interface 2266, which can include digital signal processing circuitry where necessary. The communication interface 2266 can provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication can occur, for example, through the transceiver 2268 using a radio-frequency. In addition, short-range communication can occur, such as using a Bluetooth, WiFi, or other such transceiver (not shown). In addition, a GPS (Global Positioning System) receiver module 2270 can provide additional navigation- and location-related wireless data to the mobile computing device 2250, which can be used as appropriate by applications running on the mobile computing device 2250. The mobile computing device 2250 can also communicate audibly using an audio codec 2260, which can receive spoken information from a user and convert it to usable digital information. The audio codec 2260 can likewise generate audible sound for a user, such as through a speaker, e.g., in a handset of the mobile computing device 2250. Such sound can include sound from voice telephone calls, can include recorded sound (e.g., voice messages, music files, etc.) and can also include sound generated by applications operating on the mobile computing device 2250. The mobile computing device 2250 can be implemented in a number of different forms, as shown in the figure. For example, it can be implemented as a cellular telephone 2280. It can also be implemented as part of a smart-phone 2282, personal digital assistant, or other similar mobile device.

Figure 23:
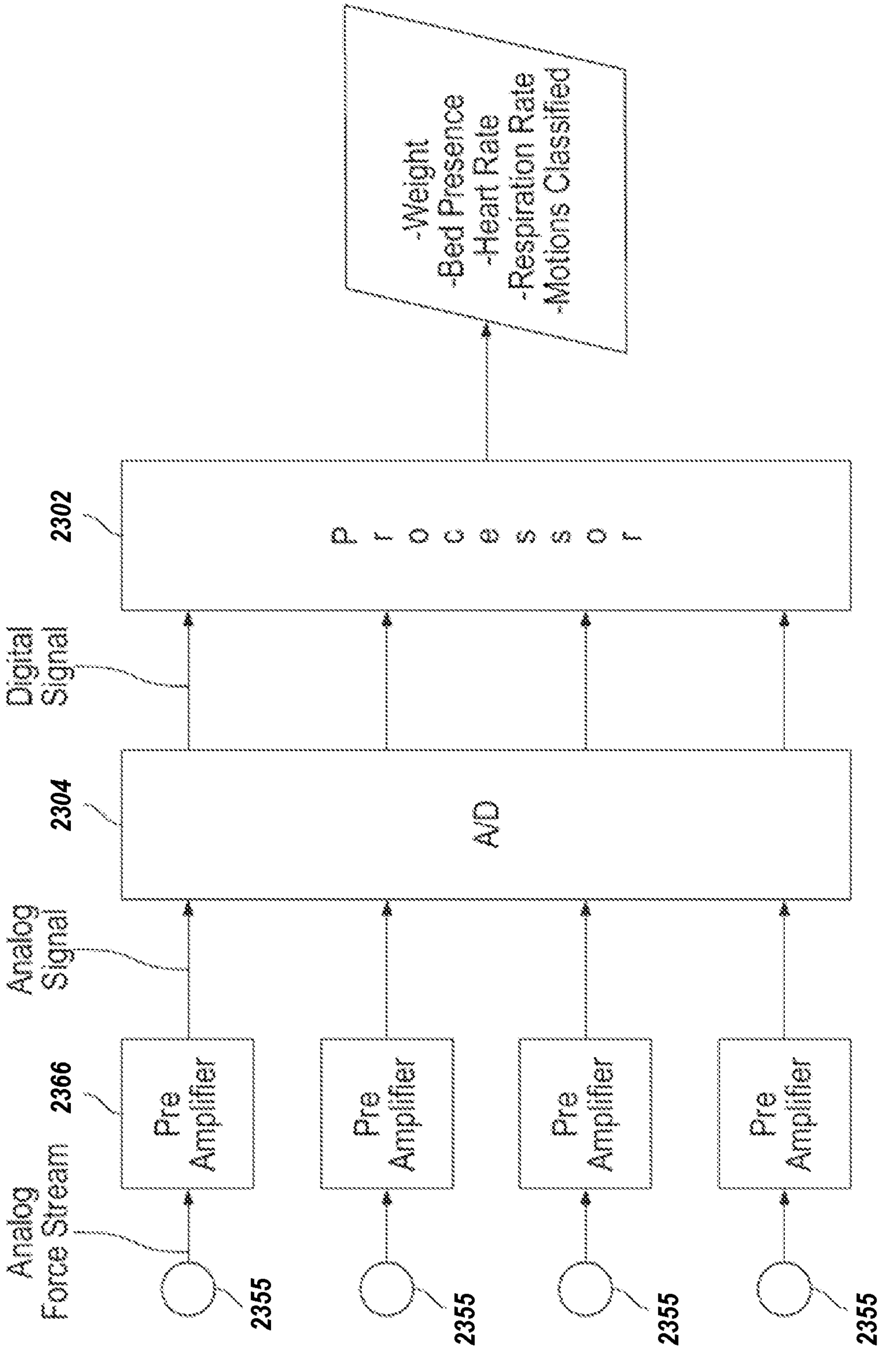
FIG. 23 is a schematic diagram of a system that can be used in conjunction with the components of the data processing system.

FIG. 23 is a schematic diagram of a system that can be used in conjunction with the components of the data processing system 800. In some implementations, the raw stream from one or more of the sensors, such as the force sensors 2355, or any other sensors, such as force sensors 255, 355, 455, 555, may not have sufficient strength to be detected, processed, and/or analyzed. In such an instance, a pre-amplifier 2366 may be used to boost the stream. In the illustrated example, the force sensors 2355 produce a force stream that is amplified by the pre-amplifier 2366. The amplified stream is then fed into an analog-to-digital converter 2304 to produce a digital stream. The digital stream is then processed by the one or more processors 2302 to determine a user parameter and/or a sleep parameter. Example user parameters and sleep parameters that can be determined include occupant presence, occupant weight, occupant heart rate, occupant respiration rate, and occupant motion categorization.

In the embodiment illustrated in FIG. 23, four force sensors 2355 each communicate with a dedicated one of four pre-amplifiers 2366, such that each of the pre-amplifiers 2366 handles only one of the force sensors 2355. In some such embodiments, each force sensor 2355 and preamplifier 2366 is housed together at a foot of a respective leg of a bed system, such as those example legs described above.

In some embodiments, the four pre-amplifiers 2366 can be replaced with a single pre-amplifier that handles all four of the force sensors 2355 (or however many force sensors are being used, whether more or fewer than four). Accordingly, all four of the force sensors 2355 can be in communication with the same pre-amplifier 2366. In some such embodiments, the single pre-amplifier 2366 can be housed at a foot of one leg of a bed system along with one of the force sensors 2355, while other legs of the bed system contain a force sensor 2355 but no pre-amplifier 2366. In other embodiments, the pre-amplifier 2366 can be located elsewhere in the bed system other than a foot of a leg.

In some embodiments, the bed system can include two pre-amplifiers 2366 (for example, one for a left side of the bed system and the other for the right side of the bed system) and more than two force sensors 2355 (such as four or six force sensors). In some such embodiments, force sensors 2355 on the left side of the bed system can all communicate with one of the two pre-amplifiers 2366 and the force sensors 2355 on the right side of the bed system can communicate with the other of the two pre-amplifiers 2366. In some such embodiments, two of the legs of the bed system can contain both a pre-amplifier and a force sensor and the other legs can include just a force sensor with no pre-amplifier. Force sensors 2355 without a dedicated pre-amplifier 2366 can be connected (e.g. via a wire) to a pre-amplifier 2366 in another leg such that that pre-amplifier 2366 serves more than one force sensor 2355, but not all force sensors 2355.

Figure 24:
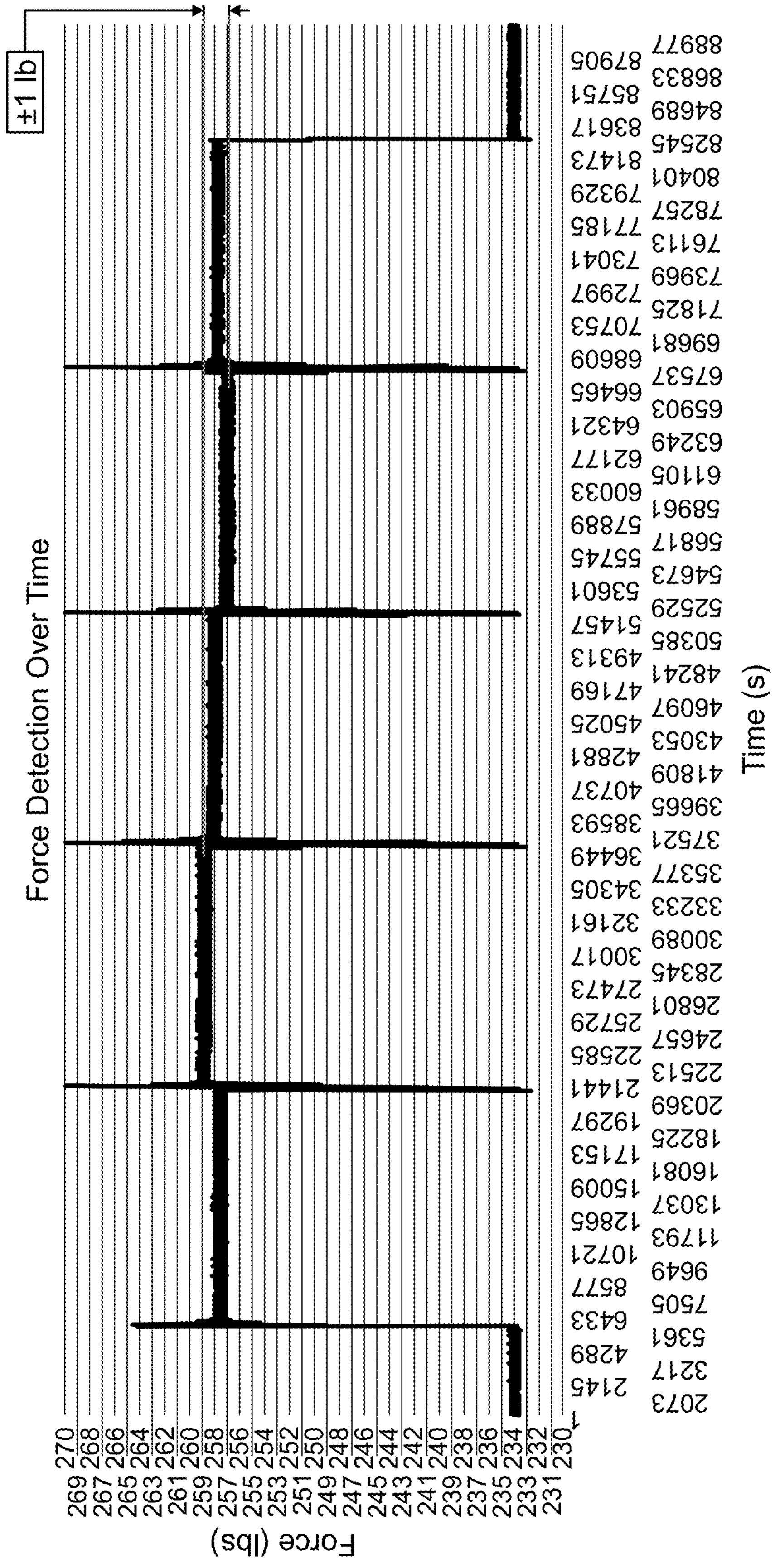
FIG. 24 is an example signal that can be produced by one or more force sensors.

FIG. 24 is an example read-out of the load stream produced by one or more force sensors (e.g., force sensors 255, 355, 455, 555). In some embodiments, the force sensor 355 can produce force reading results with plus or minus one pound of variability by being constrained to two degrees of freedom. The deformable portions 385 facilitate movement of the plate 382 to compress the force sensor 355 in response to a force applied along a vertical axis of the leg 353. The foot 383 can reduce, minimize, or eliminate the transmission of other forces to the force sensor 355, which facilitates consistent force reading results by the force sensor 355. In some embodiments, the force sensors 455 and 555 can produce force reading results with plus or minus one pound of variability by being constrained to two degrees of freedom within the legs 453, 553. As illustrated, the force sensor is able to determine the weight of a user, and can produce a consistent force reading result with plus or minus one pound of variability across multiple tests. Accordingly, the legs 253, 353, 453, and 553 and the force sensors 255, 355, 455, and 555 facilitate the acquisition of consistent and reliable force sensor readings that have minimal or no noise and capture accurate force data. This accurate data can be analyzed to generate user parameters and sleep parameters as discussed above.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input. The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet. The computing system can include clients and servers. A client and server are generally remote from each other and typically interact through a communication network. The relationship of client and server arises by virtue of computer programs running on the respective computers and having a client-server relationship to each other.

A number of aspects/embodiments of the inventions have been described. Nevertheless, it will be understood that various modifications can be made without departing from the spirit and scope of the invention. For example, in some embodiments the legs 253, 353, 453, and 553 can include components of different sizes, shapes, and orientations. Additionally, different features of different embodiments of one of the embodiments the legs 253, 353, 453, and 553 can be combined with other features of one or more other embodiments of the legs 253, 353, 453, and 553 as suitable for the application. Accordingly, other embodiments are within the scope of the following claims.

What is claimed is:

1. A bed system comprising:

a support platform; and a plurality of legs supporting the support platform, each leg of the plurality of legs comprising:

a mount positioned in the leg and connected to an inside surface of the leg;

a force sensor connected to the mount, the force sensor configured to sense a force applied to the leg;

a foot that extends around the force sensor and the mount and contacts a floor, the foot having deformable portions along a bottom of the foot and a plate portion of the foot that receives a plate that aligns with the force sensor, wherein the deformable portions are configured to facilitate movement of the plate to compress and contact the force sensor in response to a force applied to the foot along a vertical axis;

a preamplifier connected to the force sensor and positioned above the mount within the leg.

2. The bed system of claim 1, wherein the deformable portions facilitate vertical movement of the plate responsive to one or more forces applied to the leg.

3. The bed system of claim 1, wherein the foot and the mount constrain the force sensor to two degrees of freedom.

4. The bed system of claim 3, wherein the two degrees of freedom are vertical motion and rotational motion.

5. The bed system of claim 1, wherein the deformable portions extend from the plate portion of the foot and end at an offset distance from an outer edge of the bottom of the foot.

6. The bed system of claim 1, wherein a sensing surface of the force sensor is exposed below the mount to facilitate contact between the plate and the force sensor.

7. The bed system of claim 1, wherein the foot comprises a rubber material that facilitates deformation of the deformable portions.

8. The bed system of claim 1, wherein a sensing surface of the force sensor faces towards the plate and a non-sensing surface faces towards the mount.

9. The bed system of claim 1, comprising a controller in communication with the force sensor, the controller configured to:

receive a plurality of force signals from the force sensor;

analyze the plurality of force signals; and generate one or more user parameters, wherein the one or more user parameters include at least one of sleeper weight, biometrics, sleep stage, restlessness, and user presence.

10. A bed system comprising:

a foundation frame configured to support a mattress; and at least a first leg defining a vertical axis, the first leg comprising:

a leg shaft mounted to the foundation frame and extending downward from the foundation frame for supporting the foundation frame;

a leg foot connected to a distal end of the leg shaft, wherein the leg foot has a foot bottom configured to contact a floor; and a force sensor connected to the leg foot and positioned in a chamber between and defined by a bottom surface of the leg shaft and one or more protrusions of the leg foot, wherein the leg foot is configured to move with respect to the leg shaft to compress the force sensor when a force is applied to the first leg along the vertical axis.

11. The bed system of claim 10 further comprising:

a controller in communication with the force sensor, the controller configured to:

receive a plurality of force signals from the force sensor;

analyze the plurality of force signals; and generate one or more user parameters.

12. The bed system of claim 11, wherein the one or more user parameters include at least one of sleeper weight, biometrics, sleep stage, restlessness, and user presence.

13. The bed system of claim 10, wherein the force sensor is constrained to two degrees of freedom in the chamber.

14. A bed system comprising:

a support platform configured for supporting a mattress; and a plurality of legs supporting the support platform, each of the plurality of legs comprising:

a mount positioned in the leg and connected to an inside surface of the leg;

a carrier positioned below the mount and connected to the mount, the carrier and the mount defining a chamber between a bottom surface of the mount an upper surface of the carrier and a chamber surface of the carrier;

a force sensor positioned in the chamber and connected to the carrier at the chamber surface of the carrier, and the chamber constrains the force sensor to two degrees of freedom, the force sensor configured to sense a force applied along a vertical axis of the leg that compresses the force sensor in the chamber;

a preamplifier connected to the force sensor and positioned above the mount within the leg.

15. The bed system of claim 14, wherein the two degrees of freedom are vertical motion and rotational motion.

16. The bed system of claim 15, wherein the rotational motion is about a vertical axis.

17. The bed system of claim 14, wherein a sensing surface of the force sensor is exposed above the carrier to facilitate contact between the mount and the force sensor.

18. The bed system of claim 14, wherein a foot is a rubber foot that is positioned between the force sensor and a floor.

19. The bed system of claim 14, wherein all the force of the bed system translates through each of the force sensors in each of the legs.

* * * * *